(12) United States Patent
Valint, Jr. et al.

(10) Patent No.: US 10,988,610 B2
(45) Date of Patent: *Apr. 27, 2021

(54) ELECTROCHEMICAL SENSOR SYSTEM

(71) Applicant: Ascensia Diabetes Care Holdings AG, Basel (CH)

(72) Inventors: Paul Valint, Jr., Pittsford, NY (US); Doug H. Williamson, Plymouth, WI (US); Boru Zhu, Gibsonia, PA (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 16/847,883

(22) Filed: Apr. 14, 2020

(65) Prior Publication Data
US 2020/0362158 A1 Nov. 19, 2020

Related U.S. Application Data

(60) Continuation of application No. 16/238,964, filed on Jan. 3, 2019, now Pat. No. 10,655,004, which is a division of application No. 15/244,837, filed on Aug. 23, 2016, now Pat. No. 10,227,485, which is a continuation of application No. 11/666,270, filed as application No. PCT/US2005/038966 on Oct. 27, 2005, now Pat. No. 9,549,697, which is a continuation-in-part of application No. 11/201,334, filed on Aug. 11, 2005, now abandoned, which is a continuation-in-part of application No. 10/974,963, filed on Oct. 28, 2004, now abandoned.

(60) Provisional application No. 60/717,064, filed on Sep. 14, 2005, provisional application No. 60/676,453, filed on Apr. 29, 2005.

(51) Int. Cl.
| | | |
|---|---|---|
| *C08L 33/26* | (2006.01) | |
| *A61B 5/145* | (2006.01) | |
| *A61B 5/00* | (2006.01) | |
| *A61B 5/1486* | (2006.01) | |
| *C08L 33/24* | (2006.01) | |
| *G01N 27/416* | (2006.01) | |
| *A61L 31/04* | (2006.01) | |
| *A61L 31/14* | (2006.01) | |
| *G01N 27/327* | (2006.01) | |

(52) U.S. Cl.
CPC ............ *C08L 33/26* (2013.01); *A61B 5/1486* (2013.01); *A61B 5/14514* (2013.01); *A61B 5/14532* (2013.01); *A61B 5/681* (2013.01); *A61L 31/048* (2013.01); *A61L 31/145* (2013.01); *C08L 33/24* (2013.01); *G01N 27/3273* (2013.01); *G01N 27/4166* (2013.01); *C08L 2203/02* (2013.01); *Y10T 436/144444* (2015.01)

(58) Field of Classification Search
CPC .... C08L 33/26; C08L 2203/02; A61L 31/048; A61L 31/145; G01N 27/3273; G01N 27/4166; A61B 5/1486; A61B 5/14532; A61B 5/14514
See application file for complete search history.

(56) References Cited

U.S. PATENT DOCUMENTS

| | | |
|---|---|---|
| 3,305,514 A | 2/1967 | Shank |
| 3,397,192 A | 8/1968 | Frederick |
| 4,576,973 A | 3/1986 | Keil |
| 5,139,023 A | 8/1992 | Stanley |
| 5,254,338 A | 10/1993 | Sakai |
| 5,489,625 A | 2/1996 | Moriwaki |
| 5,773,146 A | 6/1998 | Lawton |
| 6,375,932 B1 | 4/2002 | Hiwatashi |
| 6,438,414 B1 | 8/2002 | Conn |
| 6,558,321 B1 | 5/2003 | Burd |
| 6,756,072 B2 | 6/2004 | Baumgart |
| 7,074,839 B2 | 7/2006 | Fansler |
| 7,169,877 B2 | 1/2007 | Baumgart |
| 7,276,247 B2 | 10/2007 | Fansler |
| 7,335,690 B2 | 2/2008 | Plaut |
| 7,342,047 B2 | 3/2008 | Lewandowski |
| 7,384,984 B2 | 6/2008 | Lewandowski |
| 7,459,489 B2 | 12/2008 | Lewandowski |
| 7,473,719 B2 | 1/2009 | Plaut |
| 7,598,298 B2 | 10/2009 | Lewandowski |
| 7,659,323 B2 | 2/2010 | Lewandowski |
| 8,224,414 B2 | 7/2012 | Kellogg |

(Continued)

FOREIGN PATENT DOCUMENTS

| | | |
|---|---|---|
| DE | 3324835 A1 | 1/1985 |
| EP | 0446636 A3 | 9/1991 |

(Continued)

OTHER PUBLICATIONS

Written Opinion corresponding to International Patent Application Serial No. PCT/US2005/038966, European Patent Office, dated Mar. 7, 2006 (6 pages).

(Continued)

*Primary Examiner* — Robert S Cabral
(74) *Attorney, Agent, or Firm* — Nixon Peabody LLP

(57) ABSTRACT

An electrochemical sensor system comprises an electrochemical sensor and a hydrogel composition. The electrochemical sensor has at least a counter electrode and a working electrode. The hydrogel composition contacts the working electrode. The hydrogel composition comprises a first monomer, a second monomer, a cross-linking agent, and a solvent. The first monomer has hydrophilic characteristics. The second monomer has hydrophobic characteristics. The ratio of the first monomer to the second monomer is from about 0.1:99.9 to about 99.9:0.1.

38 Claims, 5 Drawing Sheets

(56) References Cited

U.S. PATENT DOCUMENTS

| | | |
|---|---|---|
| 8,271,064 B2 | 9/2012 | Brenneman |
| 8,481,059 B2 | 7/2013 | Cleary |
| 8,504,131 B2 | 8/2013 | Brenneman |
| 8,728,445 B2 | 5/2014 | Cleary |
| 2002/0091312 A1 | 7/2002 | Berner |
| 2003/0104132 A1 | 6/2003 | Baumgart |
| 2004/0062759 A1 | 4/2004 | Abraham |
| 2004/0087671 A1 | 5/2004 | Tamada |
| 2004/0087714 A1 | 5/2004 | Baumgart |
| 2004/0209095 A1 | 10/2004 | Manias |
| 2005/0070688 A1 | 3/2005 | Lewandowski |
| 2005/0131148 A1 | 6/2005 | Lewandowski |
| 2005/0192370 A1 | 9/2005 | Fansler |
| 2005/0194559 A1 | 9/2005 | Lewandowski |
| 2006/0094944 A1 | 5/2006 | Chuang |
| 2006/0094945 A1 | 5/2006 | Barman |
| 2006/0165762 A1 | 7/2006 | Plaut |
| 2006/0165999 A1 | 7/2006 | Fansler |
| 2006/0167180 A1 | 7/2006 | Plaut |
| 2008/0154007 A1 | 6/2008 | Mori |
| 2008/0311670 A1 | 12/2008 | Zhu |
| 2010/0206746 A1 | 8/2010 | Zhu |
| 2016/0376431 A1 | 12/2016 | Valint |

FOREIGN PATENT DOCUMENTS

| | | |
|---|---|---|
| WO | WO 1999/039635 A1 | 8/1999 |
| WO | WO 2001/057241 A2 | 8/2001 |

OTHER PUBLICATIONS

International Search Report corresponding to International Patent Application Serial No. PCT/US2005/038966, European Patent Office, dated Mar. 7, 2006 (5 pages).

Zhong, Yuanzhen et al. "Swelling Properties of Crosslinked Vinylpyrrolidone Homopolymers and Vinylpyrrolidone/Vinyl Acetate Copolymers." Polymer Reprints, 39 (2), pp. 461-462 (1998).

ELECTROCHEMICAL SENSOR SYSTEM

CROSS-REFERENCE TO RELATED APPLICATIONS

This application is a continuation of U.S. patent application Ser. No. 16/238,964 filed Jan. 3, 2019; U.S. patent application Ser. No. 16/238,964 is a divisional of U.S. patent application Ser. No. 15/244,837 filed Aug. 23, 2016; U.S. patent application Ser. No. 15/244,837 is a continuation of U.S. patent application Ser. No. 11/666,270, filed Feb. 19, 2008; U.S. patent application Ser. No. 11/666,270 is a national stage of Application No. PCT/US2005/038966 filed Oct. 27, 2005, Application No. PCT/US2005/038966 claims priority to U.S. patent application Ser. No. 11/201,334, filed Aug. 11, 2005, U.S. patent application Ser. No. 10/974,963, filed Oct. 28, 2004, Provisional Application No. 60/717,064 filed Sep. 14, 2005; and Provisional Application No. 60/676,453 filed Apr. 29, 2005.

FIELD OF THE INVENTION

The present invention generally relates to hydrogel compositions. The hydrogel composition in one application is adapted to be used in a transdermal method of determining the concentration of an analyte (e.g., glucose).

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered.

In some existing techniques, a lancet may be used to draw fluid (e.g., blood) from a user. This fluid is then used with an instrument or meter to determine an analyte concentration. It would be desirable to eliminate the need to use a lancet, while still accurately determining the analyte concentration.

One non-invasive method for obtaining a sample without using a lancet is to use a transdermal sample of analytes found in interstitial fluid (ISF). In this method, a composition is placed on the skin and assists in facilitating the extraction of the ISF from the user skin's to a sensing instrument or meter. This composition needs to possess sufficient mechanical and thermal stability to provide a relatively static, reactive and aqueous conduct between the dermal sampling site and sensing instrument. It would be desirable to find such a composition that contains such attributes and is adapted to be used in transdermal sampling.

SUMMARY OF THE INVENTION

According to one embodiment, a hydrogel composition comprises a first monomer, a second monomer, a cross-linking agent, and a solvent. The first monomer is selected from Formula I:

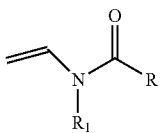

Formula I wherein
R and R1 are independently selected from H, $(C_1\text{-}C_3)$alkyl, $(C_3\text{-}C_6)$dihydroxy alkyl and $(C_2\text{-}C_6)$hydroxy alkyl; or the combination of R and R1 is selected from 1 carbon to 5 carbon atoms such that a 3-7 member heterocyclic moiety is formed.

The second monomer is selected from the group consisting of Formula II and Formula III, wherein Formula II is

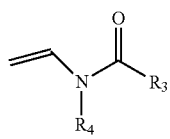

Formula II wherein
R3 and R4 are independently selected from H, $CH_3$, $(C_3\text{-}C_{18})$alkyl, $(C_3\text{-}C_7)$ cycloalkyl or aromatic moieties. The alkyl is optionally substituted with one or more substituents selected from halos, haloalkyls, cycloalkyls, nitros, cyanos, 4-8 member heterocyclic moieties. The heterocyclic moieties are optionally substituted with one or more alkyls, halos, haloalkyls, cycloalkyls, nitros, and cyanos. The cycloalkyl is optionally substituted with one or more substituents selected from alkyls, halos, haloalkyls, cycloalkyls, nitros, and cyanos. The aromatic moieties are optionally substituted with one or more substituents selected from alkyls, halos, haloalkyls, cycloalkyls, nitros, and cyanos. If R3 is H or $CH_3$, then R4 is a $(C_3\text{-}C_{18})$alkyl, a $(C_3\text{-}C_7)$ cycloalkyl or an aromatic moiety. The alkyl, cycloalkyl or aromatic moiety is optionally substituted with one or more substituents. If R4 is H or $CH_3$, then R3 is a $(C_3\text{-}C_{18})$alkyl, a $(C_3\text{-}C_7)$cycloalkyl or an aromatic moiety. The alkyl, cycloalkyl or aromatic moiety is optionally substituted with one or more substituents.

Formula III is

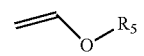

Formula III wherein
R5 is selected from $(C_3\text{-}C_{18})$alkyl, $(C_3\text{-}C_7)$ cycloalkyl or aromatic moieties. The alkyl is optionally substituted with one or more substituents selected from halos, haloalkyls, cycloalkyls, nitros, cyanos, 4-8 member heterocyclic moieties. The heterocyclic moieties are optionally substituted with one or more alkyls, halos, haloalkyls, cycloalkyls, nitros, and cyanos. The cycloalkyl is optionally substituted with one or more substituents selected from alkyls, halos, haloalkyls, cycloalkyls, nitros, and cyanos. The aromatic moieties are optionally substituted with one or more substituents selected from alkyls, halos, haloalkyls, cycloalkyls, nitros, and cyanos. The ratio of the first monomer to the second monomer is from about 0.1:99.9 to about 99.9:0.1.

According to one embodiment, an electrochemical sensor system comprises an electrochemical sensor and a hydrogel composition. The electrochemical sensor has at least a counter electrode and a working electrode. The hydrogel composition contacts the working electrode. The hydrogel composition comprises a first monomer, a second monomer, a cross-linking agent, and a solvent. The first monomer is selected from hydroxy alkyl methacrylates, acrylamide, N,N di-alkyl acrylamides, methacrylic acid, acrylic acid, methacrylate metal salts, acrylate metal salts, iticonic acid, maleic acid, methacrylamide, N,N-dialkylacrylamide, styrene sulfonic acid, styrene sulfonate metal salts, styrene carboxylic acid, styrene carboxylate metal salts, acrylamido-2-methylpropane sulfonic acid, acrylamido-2-methylpropane sulfonate metal salts, 2-vinyl N-alkylpyridinium halide, 4-vinyl N-alkylpyridinium halide, or Formula I, which is discussed above. The second monomer is selected from the group consisting of alkyl (meth)acrylates, Formula II, Formula III, and Formula IV, in which Formula II and Formula III are discussed above.

Formula IV is

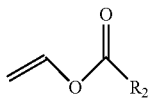

Formula IV wherein
$R_2$ is selected from $(C_1-C_{18})$alkyl, $(C_3-C_7)$cycloalkyl and aromatic moieties. The alkyl is optionally substituted with one or more substituents selected from halos, haloalkyls, cycloalkyls, nitros, cyanos, 4-8 member heterocyclic moieties. The heterocyclic moieties are optionally substituted with one or more alkyls, halos, haloalkyls, cycloalkyls, nitros, and cyanos. The cycloalkyl is optionally substituted with one or more substituents selected from alkyls, halos, haloalkyls, cycloalkyls, nitros, and cyanos. The aromatic moieties are optionally substituted with one or more substituents selected from alkyls, halos, haloalkyls, cycloalkyls, nitros, and cyanos. The ratio of the first monomer to the second monomer is from about 0.1:99.9 to about 99.9:0.1.

According to one embodiment, an electrochemical sensor system comprises an electrochemical sensor and a hydrogel composition. The electrochemical sensor has at least a counter electrode and a working electrode. The hydrogel composition contacts the working electrode. The hydrogel composition comprises a first monomer, a second monomer, a cross-linking agent, and a solvent. The first monomer is selected from Formula I, which is discussed above. The second monomer is selected from the group consisting of alkyl (meth)acrylates, Formula II, Formula III, and Formula IV, which are discussed above.

According to a further embodiment, an electrochemical sensor system comprises an electrochemical sensor and a hydrogel composition. The electrochemical sensor has at least a counter electrode and a working electrode. The hydrogel composition contacts the working electrode. The hydrogel composition comprises a first monomer, a second monomer, a cross-linking agent, and a solvent. The first monomer is selected from the group consisting of N-vinyl pyrrolidone, hydroxy alkyl methacrylates, acrylamide, and N,N di-alkyl acrylamides. The second monomer is selected from the group consisting of alkyl (meth)acrylates, N-vinyl acrylamide, vinyl esters, and vinyl ethers. The ratio of the first monomer to the second monomer is from about 0.1:99.9 to about 99.9:0.1.

According to yet another embodiment, an electrochemical sensor system comprises an electrochemical sensor and a hydrogel composition. The electrochemical sensor has at least a counter electrode and a working electrode. The hydrogel composition contacts the working electrode. The hydrogel composition comprises a first monomer, a second monomer, a cross-linking agent, and a solvent. The first monomer has hydrophilic characteristics. The second monomer has hydrophobic characteristics. The ratio of the first monomer to the second monomer is from about 0.1:99.9 to about 99.9:0.1.

According to one method, an analyte concentration is determined by placing a hydrogel composition on skin. The hydrogel composition comprises a first monomer, a second monomer, a cross-linking agent, and a solvent. The first monomer is selected from hydroxy alkyl methacrylates, acrylamide, N,N di-alkyl acrylamides, methacrylic acid, acrylic acid, methacrylate metal salts, acrylate metal salts, iticonic acid, maleic acid, methacrylamide, N,N-dialkylacrylamide, styrene sulfonic acid, styrene sulfonate metal salts, styrene carboxylic acid, styrene carboxylate metal salts, acrylamido-2-methylpropane sulfonic acid, acrylamido-2-methylpropane sulfonate metal salts, 2-vinyl N-alkylpyridinium halide, 4-vinyl N-alkylpyridinium halide, or Formula I, which is discussed above. The second monomer is selected from the group consisting of alkyl (meth)acrylates, Formula II, Formula III, and Formula IV, which are discussed above. A sensor is provided and the hydrogel composition is located generally between and coupling the skin and the sensor. The interstitial fluid is sampled to determine the analyte concentration using the sensor.

According to another method, an analyte concentration is determined. The method comprises placing a hydrogel composition on skin. The hydrogel composition comprises a first monomer, a second monomer, a cross-linking agent, and a solvent. The first monomer is selected from Formula I, which is discussed above. The second monomer is selected from the group consisting of alkyl (meth)acrylates, Formula II, Formula III, and Formula IV, which are discussed above. A sensor is provided and the hydrogel composition is located generally between and coupling the skin and the sensor. The interstitial fluid is sampled to determine the analyte concentration using the sensor.

According to a further method, an analyte concentration is determined. The method comprises placing a hydrogel composition on skin. The hydrogel composition comprises a first monomer, a second monomer, a cross-linking agent, and a solvent. The first monomer is selected from the group consisting of N-vinyl pyrrolidone, hydroxy alkyl methacrylates, acrylamide, and N,N di-alkyl acrylamides. The second monomer is selected from the group consisting of alkyl (meth)acrylates, N-vinyl acylamide, vinyl esters, and vinyl ethers. The ratio of the first monomer to the second monomer is from about 0.1:99.9 to about 99.9:0.1. A sensor is provided and the hydrogel composition is located generally between and coupling the skin and the sensor. The interstitial fluid is sampled to determine the analyte concentration.

According to a yet another method, an analyte concentration is determined. The method comprises placing a hydrogel composition on skin. The hydrogel composition comprises a first monomer, a second monomer, a cross-linking agent, and a solvent. The first monomer has hydrophilic characteristics. The second monomer has hydrophobic characteristics. The ratio of the first monomer to the second monomer is from about 0.1:99.9 to about 99.9:0.1. A sensor is provided and the hydrogel composition is located generally between and coupling the skin and the sensor. The interstitial fluid is sampled to determine the analyte concentration using the sensor.

DETAILED DESCRIPTION OF ILLUSTRATED EMBODIMENTS

Figure 1:
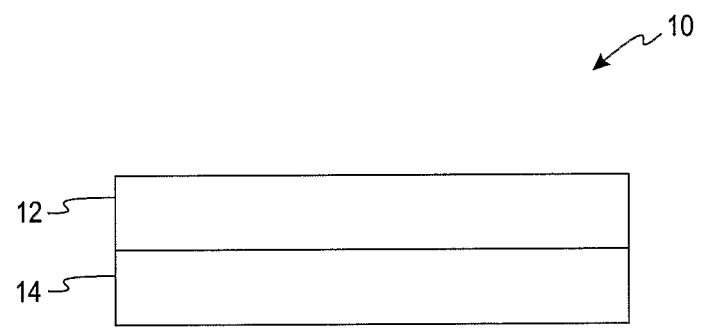
FIG. 1 is a dried hydrogel and a mechanical support according to one embodiment.

The present invention is directed to novel hydrogel compositions. The hydrogel composition comprises a first monomer, a second monomer, a cross-linking agent, and a solvent (e.g., water). The hydrogel composition is a random, copolymeric network that combines at least the first and second monomer in the form of polymeric chains. The copolymeric network is controlled to at least some extent by the volumetric percentages of the first and second monomers.

The terms identified below have the following meaning throughout:

The term "alkyl" mean linear or branched saturated carbon groups. The terms "$(C_1-C_3)$alkyl", "$(C_1-C_{18})$alkyl" and "$(C_3-C_{18})$alkyl" mean linear or branched saturated carbon groups having from 1 to about 3 carbon atoms, 1 to about 18 carbon atoms, or from about 3 to about 18 carbon atoms, respectively. Such groups include but are not limited to methyl, ethyl, n-propyl, isopropyl, n-butyl, isobutyl, sec-butyl, tert-butyl, and the like.

The term "optionally substituted" means that, unless indicated otherwise, the moiety so modified may have one or more substituents indicated. Each substituent may replace any H atom on the moiety so modified as long as the replacement is chemically possible and chemically stable. For example, a chemically unstable compound would be one where each of two substituents is bonded to a single C atom through each substituent's heteroatom. Another example of a chemically unstable compound would be one where an alkoxy group is bonded to the unsaturated carbon of an alkene to form an enol ether. When there are two substituents on any moiety, each substituent is chosen independently of the other substituent so that, accordingly, the substituents can be the same or different.

The term "cycloalkyl" means a saturated monocyclic alkyl group. The term "$(C_3-C_7)$cycloalkyl" means a saturated monocyclic alkyl group of from about 3 to about 7 carbon atoms. Such groups include, but are not limited to, cyclopropyl, cyclobutyl, cyclopentyl, cyclohexyl and cycloheptyl.

The term "$(C_3-C_6)$dihydroxy alkyl" means an alkyl group, as described above, that includes two hydroxy (—OH) constituents bonded to a saturated carbon. The $(C_3-C_6)$ dihydroxy alkyls may be straight or branched. The hydroxy constituents of the $(C_3-C_6)$dihydroxy alkyls are typically adjacent to each other. The $(C_3-C_6)$dihydroxy constituents, however, may be added at any available carbon. Such $(C_3-C_6)$dihydroxy alkyls include, but are not limited, to 2,3-dihydroxypropyl, 3,4-dihydroxybutyl, 5,6-dihydroxyhexyl, and the like.

The term "$(C_2-C_6)$hydroxy alkyl" means an alkyl group, as described above, that includes one hydroxy (—OH) constituent bonded to a saturated carbon. The $(C_2-C_6)$hydroxy alkyls may be straight or branched. The hydroxy constituent of the $(C_2-C_6)$hydroxy alkyls may be located at any available carbon. Such $(C_2-C_6)$hydroxy alkyls include, but are not limited, to 2-hydroxyethyl, 3-hydroxypropyl and the like.

The term "halo" means an atom selected from Cl, Br, and F.

The term "haloalkyl" means an alkyl group, as described above, that includes one or more halo constituent bonded to a saturated carbon. The haloalkyls may be straight or branched. The halo constituent of the haloalkyls may be located at any available carbon. Such haloalkyls include, but are not limited, to 2-chloroethyl, 3-bromopropyl, 2,2,3,3,3-pentafluoropropyl and the like.

The term "nitro" means an atom selected from —$NO_2$, cyano (—CN), —$NHCH_3$ and —$NHC_2H_5$.

The term "heterocyclic moiety" is a substance that contains a ring structure in which atoms other than carbon (e.g., sulfur, oxygen or nitrogen) are formed as part of the ring. For example, a 3-7 member heterocyclic moiety includes at least one other atom other than carbon formed as a part of the ring or backbone of a 3-7 ring structure. A 4-8 member heterocyclic moiety includes at least one other atom other than carbon formed as a part of the ring or backbone of a 4-8 ring structure.

The term "hydrophilic characteristics" means having an affinity for water or other polar solvents; readily absorbing or dissolving in water or other polar solvents.

The term "hydrophobic characteristics" means not having an affinity for water or other polar solvents; not readily absorbing or dissolving in water or other polar solvents.

The term "aromatic moiety" means a substance containing one or more benzene rings. An aromatic substituent may be monocyclic, bicyclic or tricyclic. Non-limiting examples of aromatic substituents include phenyl, benzyl, naphthyl, anthracenyl and the like.

Notations such as "(meth)acrylic acid" are used herein to denote optional methyl substitution. Thus, for example, "(meth)acrylic acid" includes methylacrylic acid and acrylic acid.

As discussed above, the hydrogel compositions include a first monomer and a second monomer. One embodiment of a first monomer is directed to a compound of Formula I, which is a N-vinyl acylamide.

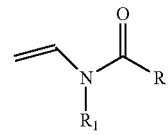

Formula I wherein
R and R1 are independently selected from H, $(C_1-C_3)$alkyl, $(C_3-C_6)$dihydroxy alkyl and $(C_2-C_6)$hydroxy alkyl; or
the combination of R and R1 is selected from 1 carbon to 5 carbon atoms such that a 3-7 member heterocyclic moiety is formed.

One non-limiting example of Formula I in which R is CH₃ and R1 is H is N-vinyl acetamide. Other examples of Formula I include R being CH₂CH₃ and R1 being H, which is N-vinyl propionamide.

Non-limiting examples of cyclic structures of Formula I include N-vinyl pyrrolidone, which is a 5 member heterocyclic compound that includes 4 carbons and 1 nitrogen in its backbone. N-vinyl pyrrolidone is shown as Compound A below:

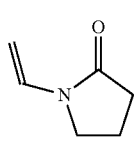

Compound A

Another example of a cyclic structure of Formula I is N-vinyl caprolactam.

It is desirable for Formula I to have hydrophilic characteristics. R and R1 are desirably independently selected such that Formula I has hydrophilic characteristics. The combination of R and R1 is also desirably selected to form a cyclic structure of Formula I that has hydrophilic characteristics.

In one embodiment, a first monomer of Formula I and a second monomer of Formula II (which is discussed below), a cross-linking agent and a solvent form a hydrogel composition. The ratio of the first monomer to the second monomer is from about 0.1:99.9 to about 99.9:0.1. More specifically, the ratio of the first monomer to the second monomer is from about 20:80 to about 80:20 and, even more specifically from about 40:60 to about 60:40. One embodiment of a second monomer is directed to a compound of Formula II, which is a N-vinyl acylamide.

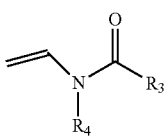

Formula II wherein
R3 and R4 are independently selected from H, CH₃, (C₃-C₁₈)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;
(C₃-C₇)cycloalkyl, wherein the cycloalkyl is optionally substituted with one or more substituents selected from alkyls, halos, haloalkyls, cycloalkyls, nitros, and cyanos; and
aromatic moieties, wherein the aromatic moieties are optionally substituted with one or more substituents selected from alkyls, halos, haloalkyls, cycloalkyls, nitros, and cyanos,
with the proviso that when R3 is H or CH₃, then R4 is (C₃-C₁₈)alkyl, (C₃-C₇)cycloalkyl or an aromatic moiety, wherein the alkyl, cycloalkyl or aromatic moiety is optionally substituted with one or more substituents,
with the proviso that when R4 is H or CH₃, then R3 is (C₃-C₁₈)alkyl, (C₃-C₇)cycloalkyl or an aromatic moiety, wherein the alkyl, cycloalkyl or aromatic moiety is optionally substituted with one or more substituents.

Examples of Formula II wherein R3 or R4 is a (C₃-C₁₈) alkyl and wherein the alkyl is optionally substituted with one or more substituents, include, but are not limited to, N-vinyl butyramide, N-vinyl valeramide, N-vinyl lauramide, N-vinyl 4-chlorobutyramide and the like.

Examples of Formula II wherein R3 or R4 is a (C₃-C₇) cycloalkyl and wherein the cycloalkyl is optionally substituted with one or more substituents, include, but are not limited to, N-vinyl cyclohexylcarboxamide, N-vinyl cyclopentylcarboamide, N-vinyl 4-bromocyclohexylcarboxamide and the like.

Examples of Formula II wherein R3 or R4 is an aromatic moiety and wherein the aromatic moiety is optionally substituted with one or more substituents, include, but are not limited to, N-vinyl benzamide, N-vinyl 4-nitrobenzamide, N-vinyl naphthamide and the like.

It is desirable for Formula II to have hydrophobic characteristics. R3 and R4 are desirably independently selected such that Formula II has hydrophobic characteristics.

In another embodiment, a first monomer of Formula I and a second monomer of Formula III (which is discussed below), a cross-linking agent and a solvent form a hydrogel composition. Another embodiment of a second monomer is directed to a compound of Formula III, which is a vinyl ether.

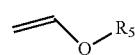

Formula III wherein
R5 is selected from (C₃-C₁₈)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;
(C₃-C₇)cycloalkyl, wherein the cycloalkyl is optionally substituted with one or more substituents selected from alkyls, halos, haloalkyls, cycloalkyls, nitros, and cyanos; and
aromatic moieties, wherein the aromatic moieties are optionally substituted with one or more substituents selected from alkyls, halos, haloalkyls, cycloalkyls, nitros, and cyanos.

Examples of Formula III wherein R5 is a (C₃-C₁₈)alkyl and wherein the alkyl is optionally substituted with one or more substituents, include, but are not limited to, vinyl propyl ether, vinyl hexyl ether, vinyl dodecyl ether, vinyl 4-chlorobutyl ether and the like.

Examples of Formula III wherein R5 is a (C₃-C₇)cycloalkyl and wherein the cycloalkyl is optionally substituted with one or more substituents, include, but are not limited to, vinyl cyclohexyl ether, vinyl cyclopentyl ether, vinyl 4-bromocyclohexyl ether and the like.

Examples of Formula III wherein R5 is an aromatic moiety and wherein the aromatic moiety is optionally substituted with one or more substituents, include, but are not limited to, vinyl phenyl ether, vinyl 4-nitrophenyl ether, vinyl 2-naphthyl ether and the like.

When the first and second monomers are mixed with a solvent (e.g., water), the structural integrity of the materials may not be as strong as desired. This especially may be the situation if the first and second monomers are mixed with a large amount of solvent. To further increase the mechanical strength, a cross-linking agent is added to the first monomer and the second monomer.

Non-limiting examples of cross-linking agents that may be used include, but are not limited to, the following: multifunctional vinyl ethers, divinylbenzenes, multifunctional acrylates, and multifunctional acrylamides. To be a desirable cross-linking agent with the first and second monomers, the cross-linking agent must be of a geometry that can connect the two polymer chains.

According to one embodiment, a cross-linking compound of Formula V (multifunctional vinyl ether) may be used.

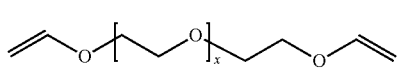

Formula V wherein "x" is from 0 to about 4. In Formula V, the "x" assists in determining properties of the cross-linking compound. Specifically, the greater the "x" component of Formula V, the better elasticity and tear strength of Formula V. By improving the elasticity and tear strength, the amount of solvent added to form the hydrogel can be greater.

An example of a multifunctional vinyl ether that may be used as a cross-linking agent is diethylene glycol divinyl ether acrylate, which is shown as Compound B below.

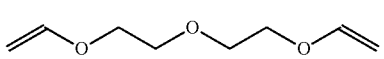

Compound B

It is contemplated that other multifunctional vinyl ethers may be used as a cross-linking agent such as triethylene glycol divinyl ether, and tetra(ethylene glycol) divinyl ether.

According to another embodiment, a cross-linking compound of Formula VI (divinylbenzene) may be used.

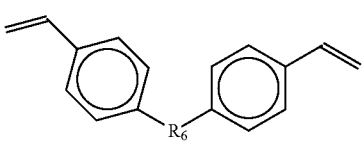

Formula VI wherein R6 is selected from $CH_2$, O, or $CH_2$—$CH_2$.

An example of a multifunctional acrylate to be used as a cross-linking agent is ethylene glycol dimethacrylate (EGDMA), which is shown as Compound C below.

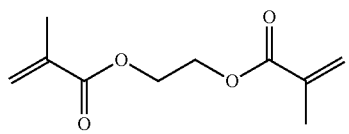

Compound C

It is contemplated that other multifunctional acrylates may be used as a cross-linking agent such as polyethylene glycol diacrylates, diethylene glycol dimethacrylate, diethylene glycol diacrylate, ethylene glycol diacrylate, and 1,3-dihydroxypropyldimethacrylate.

An example of a multifunctional acrylamide that may be used as a cross-linking agent is N,N' methylene biaacrylamide, which is shown as Compound D below.

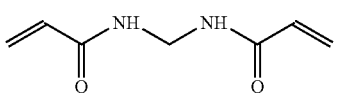

Compound D

It is contemplated that other multifunctional acrylamides may be used as a cross-linking agent.

The copolymeric network composition generally comprises from about 0.01 to about 10 vol. % cross-linking agent. The copolymeric network composition is defined herein as including the first monomer, the second monomer, the cross-linking agent, and other components to be discussed below prior to curing. The copolymeric network composition as defined does not include the solvent (e.g., water). More specifically, the polymeric network composition comprises from about 0.1 to about 1 vol. % cross-linking agent.

To assist in the polymerization, a photo-initiator may be added to the first monomer, the second monomer and the cross-linking agent. One example of a photo-initiator is 2-Hydroxy-4'-(2-hydroxyethoxy)-2-methylpropiophenone marketed as Irgacure® 2959 by Ciba Specialty Chemicals Pty, Ltd. It is contemplated that other photo-initiators may be added. The polymer network composition generally comprises from 0.0001 to about 5 wt. % photo-initiator.

The first and second monomers are mixed with a solvent. One example of a solvent that is typically used is water. Another example of a solvent is a water mixture. It is contemplated that other solvents may be used in the present invention. The amount of water may vary and is largely dependent on the amount of the first monomers and second monomers present in the hydrogel composition. It is contemplated that other materials may be added to the hydrogel composition of the first monomer, second monomer, cross-linking agent, and the solvent.

After the cross-linking agent has been added, the first and second monomers form a cross-linked, copolymer network. To achieve polymerization of the first and second monomers with the cross-linking agent, the polymerization may be initiated by methods such as, for example, ultraviolet (UV) radiation with the addition of an UV initiator), thermal initiation (with the addition of a thermal initiator), γ-ray, and electron beam. To assist in the polymerization, a photo-initiator may be added to the first monomer, second monomer and the cross-linking agent. The copolymeric network in one method is soaked in a solvent (e.g., water) to create a hydrogel composition.

In one embodiment, the hydrogel composition may be adapted to serve as an interface between skin and a sensor (e.g., an electrochemical sensor). In one method, the sensor determines the concentration of the desired analyte in the ISF (interstitial fluid) using the hydrogel composition. Analytes that may be measured include glucose, lipid profiles (e.g., cholesterol, triglycerides, LDL and HDL), microalbumin, hemoglobin $A_{1C}$, fructose, lactate, or bilirubin. It is contemplated that other analyte concentrations may be determined. As used within this application, the term "concentration" refers to an analyte concentration, activity (e.g., enzymes and electrolytes), titers (e.g., antibodies), or any other measure concentration used to measure the desired analyte.

The hydrogel composition, which is to be used as an interface between skin and a sensor in this embodiment, comprises a first monomer, a second monomer, a cross-linking agent, and a solvent (e.g., water). The hydrogel composition is a random, copolymeric network that combines at least the first and second monomer in the form of polymeric chains. The copolymeric network is controlled to at least some extent by the volumetric percentages of the first and second monomers. In this application, it is advantageous for the hydrogel composition to have a balance between gel strength and flexibility. It is also desirable for the hydrogel composition to have a desirable signal strength.

The first monomer is adapted to provide a hydrophilic character to the hydrogel composition. The first monomer includes the compounds of Formula I (N-vinyl acylamide), which is discussed in more detail above.

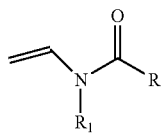

Formula I wherein
R and R1 are independently selected from H, $(C_1-C_3)$alkyl, $(C_3-C_6)$dihydroxy alkyl and $(C_2-C_6)$hydroxy alkyl; or
the combination of R and R1 is selected from 1 carbon to 5 carbon atoms such that a 3-7 member heterocyclic moiety is formed.

It is contemplated that other first monomers may be used including hydroxy alkyl methacrylates, acrylamide, N,N di-alkyl acrylamides, methacrylic acid, acrylic acid, methacrylate metal salts, acrylate metal salts, iticonic acid, maleic acid, methacrylamide, N,N-dialkylacrylamide, styrene sulfonic acid, styrene sulfonate metal salts, styrene carboxylic acid, styrene carboxylate metal salts, acrylamido-2-methylpropane sulfonic acid, acrylamido-2-methylpropane sulfonate metal salts, 2-vinyl N-alkylpyridinium halide, or 4-vinyl N-alkylpyridinium halide.

An example of a hydroxy alkyl methacrylate that may be used as a first monomer is hydroxy ethyl methacrylate, which is shown as Compound E below.

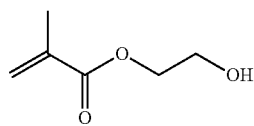

Compound E

It is contemplated that other hydroxy alkyl methacrylates may be used as the first monomer such as hydroxy propyl methacrylate, hydroxyethylacrylate, 2,3-dihydroxypropylmethacrylate, and 2,3-dihydroxypropylacrylate.

Acrylamide, which may be used as the first monomer, is shown as Compound F below.

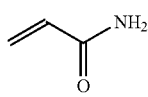

Compound F

An example of a N,N di-alkyl acrylamide that may be used as a first monomer is N,N di-methyl acrylamide, which is shown as Compound G below.

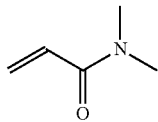

Compound G

It is contemplated that other N,N di-alkyl acrylamides may be used as the first monomer such as N,N di n-propylacrylamide, N-isopropyl acrylamide, and N,N-dimethylmethacrylamide.

According to another embodiment, the first monomer may be methacrylic acid, which is shown as Compound H below:

Compound H

The second monomer is adapted to provide mechanical strength to the hydrogel composition. The second monomer is adapted to also provide a hydrophobic character to the hydrogel composition. By providing a hydrophobic character to the hydrogel composition, the amount of solvent (e.g., water) is better controlled.

In one embodiment, a second monomer is directed to a compound of Formula II (N-vinyl acylamide), which is discussed in more detail above.

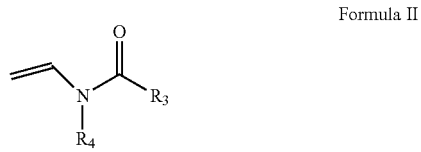

Formula II wherein
R3 and R4 are independently selected from H, $CH_3$, $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, with the proviso that when R3 is H or $CH_3$, then R4 is $(C_3-C_{18})$alkyl, $(C_3-C_7)$cycloalkyl or an aromatic moiety, wherein the alkyl, cycloalkyl or aromatic moiety is optionally substituted with one or more substituents, with the proviso that when R4 is H or $CH_3$, then R3 is $(C_3-C_{18})$alkyl, $(C_3-C_7)$cycloalkyl or an aromatic moiety, wherein the alkyl, cycloalkyl or aromatic moiety is optionally substituted with one or more substituents.

In another embodiment, a second monomer is directed to a compound of Formula III (vinyl ether), which is discussed in more detail above.

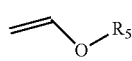
Formula III wherein
R5 is selected from $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos.

A further embodiment of a second monomer is directed to a compound of Formula IV, which is a vinyl ester.

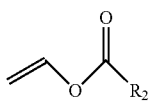
Formula IV wherein
R2 is selected from $(C_1-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos.

Examples of Formula IV wherein R2 is a $(C_1-C_{18})$alkyl and wherein the alkyl is optionally substituted with one or more substituents, include, but are not limited to, 2-chloroethyl, 3-bromopropyl, 2,2,3,3,3-pentafluoropropyl and the like.

Examples of Formula IV wherein R2 is a $(C_3-C_7)$cycloalkyl and wherein the cycloalkyl is optionally substituted with one or more substituents, include, but are not limited to, cyclopentyl, cyclohexyl, 2-chlorocyclohexyl, 4-bromocyclohexyl and the like.

Examples of Formula IV wherein R2 is an aromatic moiety and wherein the aromatic moiety is optionally substituted with one or more substituents, include, but are not limited to, vinyl benzoate, vinyl phenylacetate, vinyl 4-bromobenzoate, vinyl 4-nitrobenzoate, vinyl 1-naphthanoate, vinyl 2-naphthanoate and the like.

Vinyl esters, such as vinyl acetate or vinyl laurate, may be used as a second monomer. Vinyl acetate is shown below as Compound J, while vinyl laurate is shown as Compound K.

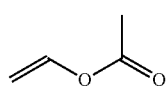
Compound J

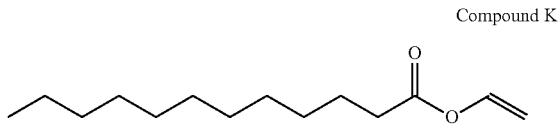
Compound K

It is contemplated that other vinyl esters may be used as the second monomer such as vinyl propionate and vinyl butyrate. It is desirable for Formula IV to have hydrophobic characteristics. R2 is desirably selected such that Formula IV has hydrophobic characteristics.

In addition to the second monomers being formed from Formulas II-IV, it is contemplated that the second monomer may further include, but is not limited to, alkyl (meth) acrylates, which includes alkyl methacrylates and alkyl acrylates. An example of an alkyl methacrylate that may be used as a second monomer is methyl methacrylate, which is shown as Compound L below.

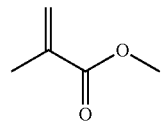
Compound L

It is contemplated that other alkyl methacrylates may be used as the second monomer such as ethyl methacrylate, propyl methacrylate, butyl methacrylate, pentyl methacrylate, hexyl methacrylate, heptyl methacrylate, octyl methacrylate, 2-ethylhexyl methacrylate, nonyl methacrylate, decyl methacrylate, undecyl methacrylate, and dodecyl methacrylate.

The ratio of the first monomer to the second monomer is from about 0.1:99.9 to about 99.9:0.1. More specifically, the ratio of the first monomer to the second monomer is from about 80:20 to about 20:80 and, even more specifically from about 60:40 to about 40:60.

One example of a copolymer network using a first monomer and a second monomer is shown below in Formula M:

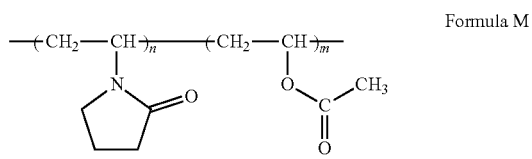
Formula M

The first monomer used in Formula M is N-vinyl pyrrolidone and the second monomer used in Formula M is vinyl acetate. The "n" and m" in Formula M represent potential repeat monomer units, in which "n" and "m" are greater than or equal to 1. The "n" and "m" of Formula M are dependent on the ratio of the first monomer to the second monomer present. It is contemplated that other combinations of the first monomers and second monomers disclosed above may be used in forming hydrogel compositions.

The copolymeric network composition generally comprises from about 0.01 to about 10 vol. % cross-linking agent. As discussed above, the copolymeric network composition is defined herein as including the first monomer, the second monomer, the cross-linking agent, and other components to be discussed below prior to curing. The copolymeric network composition as defined does not include the solvent (e.g., water). More specifically, the polymeric network composition comprises from about 0.1 to about 1 vol. % cross-linking agent.

As discussed above, to assist in the polymerization, a photo-initiator may be added to the first monomer, the second monomer and the cross-linking agent. One example of a photo-initiator is 2-Hydroxy-4'-(2-hydroxyethoxy)-2-methylpropiophenone marketed as Irgacure® 2959 by Ciba Specialty Chemicals Pty, Ltd. It is contemplated that other photo-initiators may be added.

The first and second monomers are mixed with a solvent. One example of a solvent that is typically used is water. Another example of a solvent is a water mixture. It is contemplated that other solvents may be used in the present invention. In applications that determine analyte concentration, however, the solvent needs to be substantially biocompatible with the skin. The amount of water may vary and is largely dependent on the amount of the first polymers and second polymers present in the hydrogel composition.

It is contemplated that other materials may be added to the hydrogel composition of the first monomer, second monomer, cross-linking agent, and the solvent. For example, an electrolyte may be added to the hydrogel composition. Depending on the application of the hydrogel composition, the electrolyte may perform multiple functions. First, the electrolyte is a chemical compound that ionizes when dissolved to produce an electrically-conductive medium. Second, the electrolyte desirables contains a high salt concentration that when used in applications contacting the skin assists in exerting osmotic pressure on the skin. By exerting osmotic pressure on the skin, the electrolyte assists in driving out the interstitial fluid (ISF) that contains the analyte. Non-limiting examples of electrolytes that may be used include sodium and potassium salts of chloride, phosphate, citrate, acetate and lactate.

The solution may further include an enzyme to assist in determining the analyte concentration. Depending on the analyte, an enzyme may assist in converting the analyte into a species amenable to detection, such as electrochemical detection. One example of an enzyme that may be used in determining glucose is glucose oxidase. It is contemplated that other enzymes may be used such as glucose dehydrogenase. If other analytes are of interest, an appropriately selected enzyme may assist in determining the concentration of that analyte. The enzyme, if used, is typically added after curing of the first monomer and the second monomer. The curing of the first and second monomers typically involves using thermal stress or applying electromagnetic radiation, which may have a negative effect on the activity of the enzyme. It is contemplated, however, that the enzyme may be mixed with the first and second monomers prior to curing.

The solution may further include a permeation enhancer. Permeation enhancers are desirable in applications in which the hydrogel composition is applied to the skin. The permeation enhancer assists in opening up the pores of the skin. Non-limiting examples of permeation enhancers that may be used include, but are not limited to, squalene, unsaturated fatty acids, glycerol derivatives of fatty alcohols, dimethylsulfoxide, and alkyl esters of fatty acids.

Other materials that may be added to the hydrogel composition include biocides, humectants, surfactants, and combinations thereof. Biocides assist in exhibiting bacterial growth. Non-limiting examples of biocides that may be used include the Paraben series of preservatives, sodium benzoate, benzalkonium chloride, and trialkyl amines.

Humectants assist in applications in which it is desirable to keep the skin moist. Non-limiting examples of humectants that may be used include glycerol, hexylene glycol and sorbitol, maltitol, polydextrose, propylene glycol, lactic acid, and lactate metal salts. Surfactants assists in coupling the hydrogel composition with the skin to obtain an improved contact therebetween. Non-limiting examples of surfactants that may be used include alkyl phenols such as TRITON® X-100 (octyl phenol ethoxylate having a molecular formula of $C_{14}H_{22}O$ $(C_2H_4O)_n$ in which an average "n" is 9 or 10), and sorbitol and sorbitol derivatives such as the TWEEN™ series.

If used in an electrochemical application, the hydrogel composition may be dried on the electrode surface and reconstituted prior to its use. When reconstituting, a solvent to be added may include an electrolyte.

In an electrochemical application, the hydrogel composition generally has a thickness of from about 0.1 mil to about 100 mils and, more specifically, has a thickness of from about 1 mil to about 30 mils. The surface area of the electrochemical sensor covered by the hydrogel composition in one embodiment is from about 0.1 to about 100 $cm^2$.

The hydrogel composition possesses sufficient mechanical and thermal stability to provide a relatively static, reactive, and aqueous conduit between the dermal sampling site and the sensor. More specifically, it is desirable for the hydrogel composition to have physical uniformity and flexibility, and mechanical stability against shear force. In selected applications, it may be desirable for the hydrogel composition to maintain a water content of from about 50 to about 90 wt. % for a desired duration (e.g., from about 24 to about 72 or more hours).

In addition, the hydrogel composition possesses high hydrophilicity to resist dehydration during extended use. By reducing or substantially eliminating dehydration, the transport properties of the hydrogel composition are not altered. It is also desirable for the hydrogel composition to maintain the porosity of the skin. The hydrogel composition also desirably displays a relatively high degree of compressibility to assist in securing good skin/sensor connectivity or skin adhesiveness.

It is also desirable for the hydrogel composition to have porosity large enough for enzyme entrapment. For example, in some applications involving the determination of glucose concentration, it is desirable for the hydrogel composition to provide a matrix for glucose oxidase (GO) and a diffusion passage for glucose and hydrogen peroxide.

After the cross-linking agent has been added, the first and second monomers form a cross-linked, copolymer network. To achieve polymerization of the first and second monomers with the cross-linking agent, the polymerization may be initiated by methods such as, for example, ultraviolet (UV) radiation (e.g., high-intensity UV radiation), thermal initiation (e.g., freeze-thaw cycling), γ-ray, and electron beam. To assist in the polymerization, a photo-initiator may be added to the first monomer, second monomer and the cross-linking agent.

The copolymeric network in one method is soaked in a solvent (e.g., water) to create a hydrogel composition. The solvent may include the above discussed components such as electrolytes, enzymes, permeation enhancers, biocides, humectants, surfactants, and combinations thereof. It is contemplated that the electrolytes, enzymes, permeation enhancers, biocides, humectants, surfactants and combinations thereof may be added separately from the solvent to the copolymeric network.

In one method, the hydrogel composition is dried to remove the solvent and form a dried copolymeric network or dried hydrogel composition. The dried hydrogel composition may be in the form of film. The dried hydrogel composition may further include a mechanical support. The mechanical support assists in providing mechanical strength to the dried hydrogel composition film. Examples of mechanical supports include polymeric mesh, woven fabric, non-woven fabric, cellulose (e.g., paper), or combinations thereof. Examples of cellulose materials include commercially available paper (e.g., paper wipes, paper towels or filter paper) or cellulosic cloth. It is contemplated that other mechanical supports may be used with the dried hydrogel composition film.

Generally, there is from about 10 to about 90 wt. % cellulose matrix with the remainder being the copolymeric network. Thus, in one embodiment, there is 10 wt. % cellulose matrix and 90 wt. % copolymeric network.

In one embodiment, the copolymeric network is absorbed into the porous cellulose matrix. For example, a graft co-polymerization reaction may occur between the first and second monomers onto a porous cellulose matrix. This reaction may be initiated by using high-energy radiation, chemical initiation and ultraviolet (UV) radiation in the presence of photo-initiators.

One example of a hydrogel composition is shown in FIG. 1 with a dried hydrogel film system 10 including a dried hydrogel composition film 12 and a mechanical support 14. It is contemplated that the mechanical support may be more than one layer. According to another embodiment, the mechanical support may be embedded within the hydrogel composition.

In one process, the dried hydrogel composition film may be reconstituted with a solvent (e.g., water). The hydrogel composition, including the copolymeric network and the solvent, may comprise from about 1 to about 99 vol. % water.

In one method, the hydrogel composition is used to assist in determining an analyte concentration of interstitial fluid (ISF) with a sensor. More specifically, the hydrogel composition is adapted to serve as an interface generally between and coupling the skin and the sensor. In this method, the sensor determines the concentration of the desired analyte from a sampling of the ISF. In one embodiment, the sensor is an electrochemical sensor. An example of an electrochemical sensor includes a standard, three-electrode potentiostat utilizing a catalytic, platinum-containing working electrode. It is contemplated that other electrochemical sensors may be used including those with fewer electrodes such as a two electrode electrochemical sensor, which includes a counter electrode and a working electrode. It is also contemplated that other sensors may be used such as optical sensors.

Figure 2:
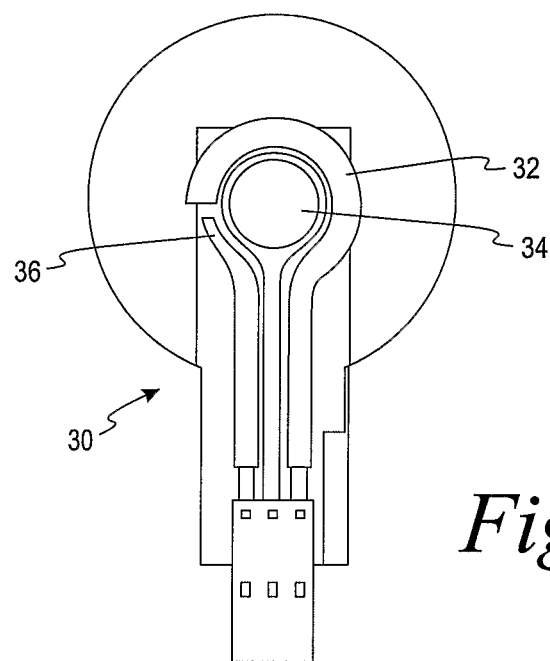
FIG. 2 is an electrochemical sensor according to one embodiment.

Referring to FIG. 2, an electrochemical sensor is shown according to one embodiment. An electrochemical sensor 30 includes a counter electrode 32, a working electrode 34, and a reference electrode 36. One specific example of such an electrochemical sensor includes a carbon counter electrode, a platinum working electrode, and a silver/silver chloride reference electrode. It is contemplated that the counter, working and reference electrodes may be made of other materials.

Figure 3:
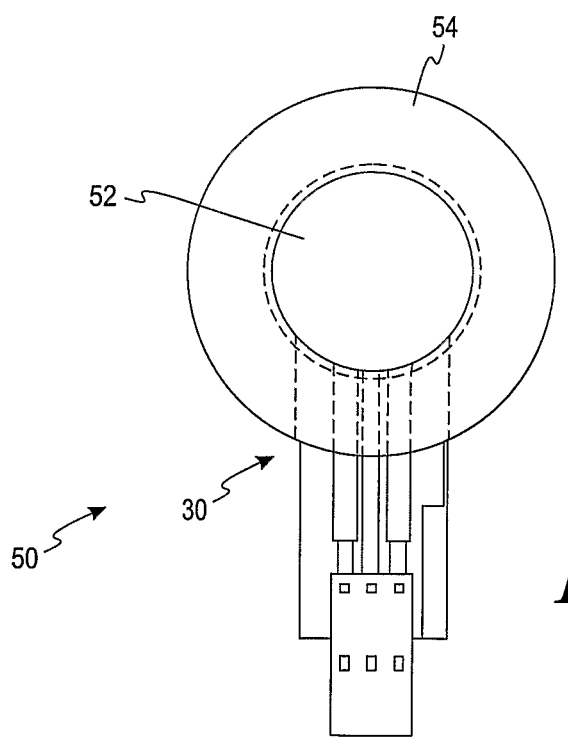
FIG. 3 is an electrochemical sensor system including the electrochemical sensor of FIG. 2.

As shown in FIG. 3, the electrochemical sensor system 50 includes the electrochemical sensor 30 of FIG. 2, a dried hydrogel film 52 and an adhesive ring 54. The dried hydrogel film 52 includes a hydrogel composition such as those described above in the absence of a solvent. In this embodiment, the adhesive ring 54 has two functions: (a) to cover a portion of the dried hydrogel film 52 and secure it to the electrochemical sensor 30; and (b) to secure the electrochemical sensor system 50, including the dried hydrogel film 52, to the skin.

In one method, a hydrogel composition is added to the skin. The hydrogel composition may be located at a skin site such as the volar forearm between the wrist and elbow. It is contemplated that the hydrogel composition may be located at other skin sites such as the abdomen. The skin is then pre-treated in this method to increase the skin permeability. One example of pre-treating is to use ultrasound energy to disrupt the lipid bilayer of the stratum corneum so as to increase the skin permeability. By increasing the skin permeability, the amount of interstitial fluid (ISF) used in transdermal sampling is increased. This results in improved sampling of the analytes of interest (e.g., glucose) found in the ISF. A sensor determines the concentration of the desired analyte after contacting the hydrogel composition and the ISF.

One non-limiting source of an ultrasound energy system is Sontra SonoPrep® ultrasonic skin permeation system marketed by Sontra Medical Corporation. The SonoPrep® system applies relatively low frequency ultrasonic energy to the skin for a limited duration (from about 10 to 20 seconds). The ultrasonic horn contained in the device vibrates at about 55,000 times per second (55 KHz) and applies energy to the skin through the liquid-coupling medium to create cavitation bubbles that expand and contract in the coupling medium.

In another method, a hydrogel composition is added to the skin from an electrochemical sensor system (e.g., electrochemical sensor system 50). The skin is then pre-treated to increase the skin permeability. One example of pre-treating is to use ultrasound energy as discussed above using for, example, Sontra's SonoPrep® ultrasonic skin permeation system marketed by Sontra Medical Corporation. The electrochemical sensor determines the concentration of the desired analyte after contacting the hydrogel composition and the ISF.

EXAMPLES

Example 1

The glucose concentration was determined using non-invasive testing. The method for generating the plots shown in FIGS. 4a,b was as follows.

A copolymeric mixture included a first monomer (N-vinyl pyrrolidone), a second monomer (vinyl acetate), a photo-initiator (2-Hydroxy-4'-(2-hydroxyethoxy)-2-methylpropiophenone) marketed as Irgacure® 2959 by Ciba Specialty Chemicals Pty Ltd., and a cross-linking agent (diethylene glycol divinyl ether). The copolymeric mixture included 50 parts N-vinyl pyrrolidone, 50 parts vinyl acetate, 0.5 parts Irgacure® 2959, and 0.5 parts diethylene glycol divinyl ether. The first monomer, second monomer, photo-initiator and cross-linking agent were mixed. The copolymeric mixture was bubbled with nitrogen ($N_2$) for about 5 minutes. The copolymeric mixture was then placed under an ultraviolet lamp for about 2.25 hours. The copolymeric mixture was then removed and stored in a refrigerator.

The copolymeric mixture was cured to form a dried copolymeric film. The dried copolymeric film was purified by rinsing twice in hot deionized water at 80° C. for 2 hours. The copolymeric film was air cooled to reform the dried copolymeric film.

The dried copolymeric film was mixed with a solution at 4° C. for over 16 hours to form a hydrogel film. The solution, which was previously prepared, was a phosphate-buffered saline solution that contained 5 wt. % glucose oxidase enzyme. The only other additive that was included in this solution was a surfactant (0.05 wt. % Triton® X-100).

The hydrogel film was cut to the desired size and dried down on the working area of an electrochemical sensor system. The dried hydrogel film on the electrochemical sensor was reconstituted with a buffered solvent (phosphate buffered saline) to form a hydrogel composition. The hydrogel composition was applied to the volar forearm between the wrist and the elbow at three different locations. Forearm Site 1 was closer to the wrist, Forearm Site 3 was closer to the elbow, and Forearm Site 2 was located between Forearm Sites 1 and 3.

The volar forearm skin at Forearm Sites 1-3 was pretreated by applying ultrasound energy thereto. The glucose oxidase enzyme in the hydrogel composition contacted the skin and the interstitial fluid (ISF) that contained glucose. The glucose oxidase enzyme assisted in converting the glucose in the ISF into peroxide. In response to detecting the peroxide, electrical current from the electrochemical sensor was generated. The electrical current corresponds to the glucose concentration in the ISF.

The electrical current was measured for each of Forearm Sites 1-3 over a period of time. The actual glucose concentrations were also measured over the same time period using a ANALOX—Glucose Analyser GM 10 marketed by Analis, which was the Comparative Method. This is labeled "Plasma Glucose" in FIGS. 4a, 4b.

Figure 4A:
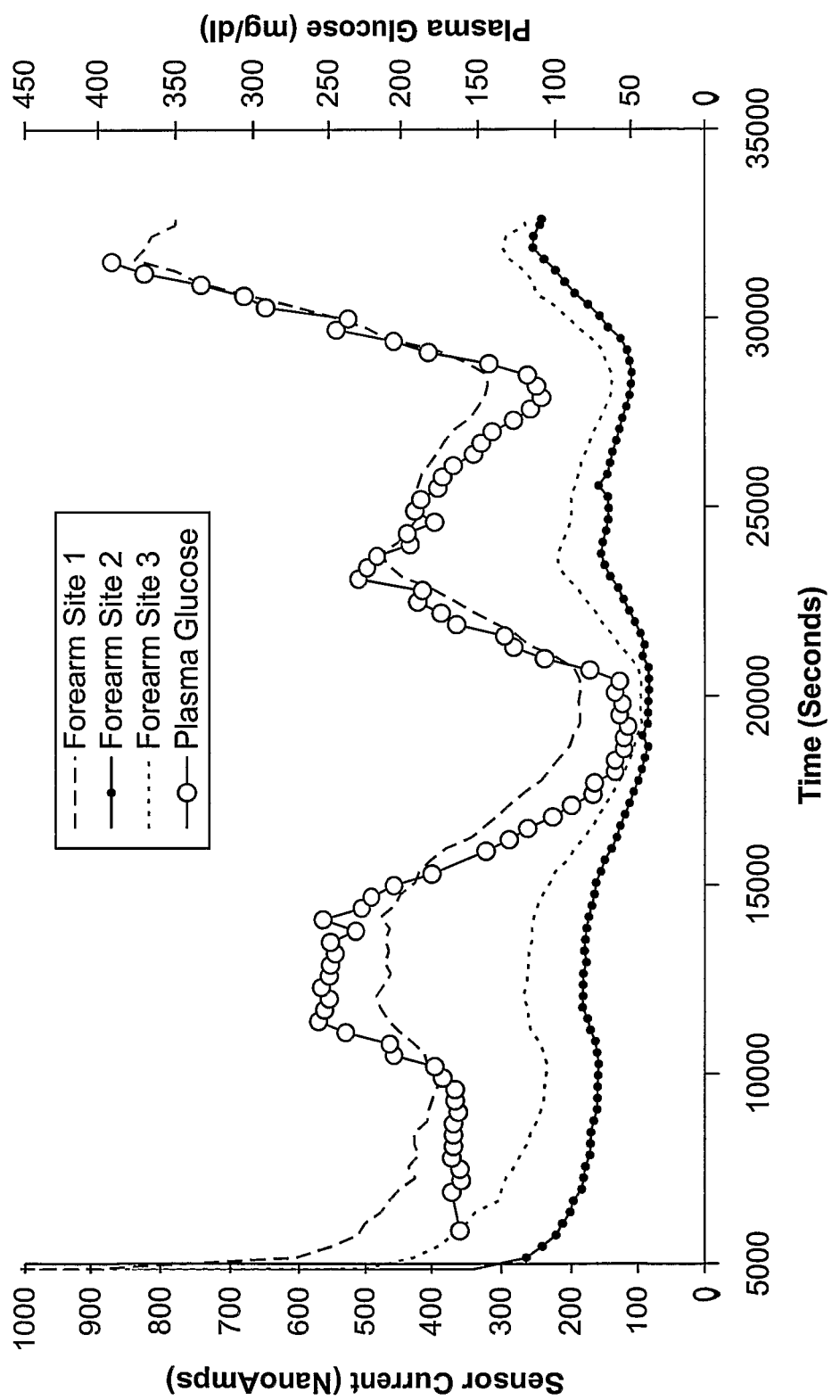
FIG. 4a is a graph plotting current, glucose concentration versus time.
Figure 4B:
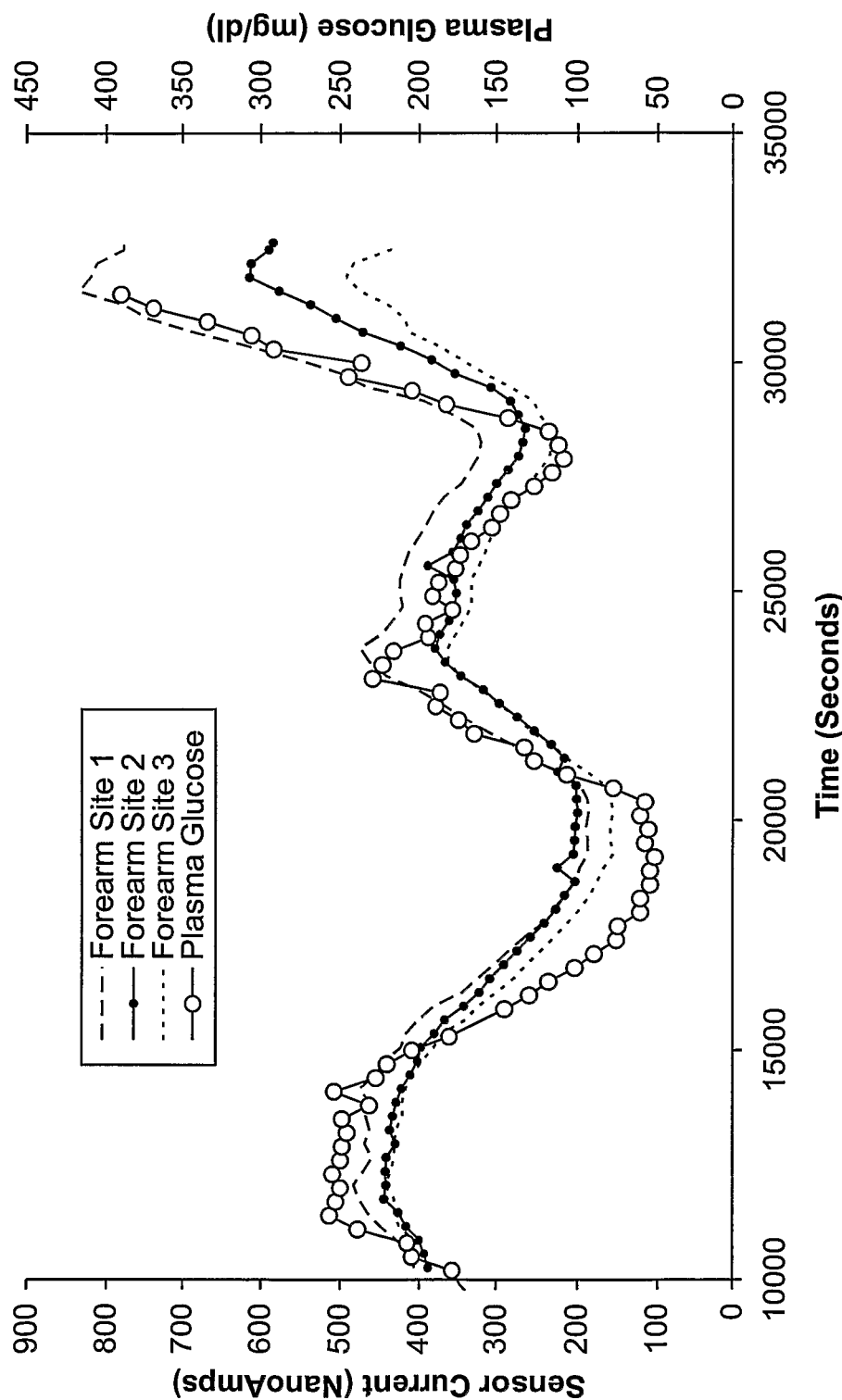
FIG. 4b is the graph of FIG. 4a plotting current, glucose concentration versus time that has been normalized.

Referring to FIG. 4a, the electrical current (in nano amps) determined by the above method using Forearm Sites 1-3 and the Comparative Method (labeled Plasma Glucose in FIG. 4a) were plotted versus time (in seconds). Additionally, the plot of FIG. 4a included glucose in mg/dL, which correlates to the measured electrical current. To better compare the same, the readings of Forearm Sites 2 and 3 were normalized relative to the highest observed sensor signal current. The normalized readings of Forearm 2 and 3 are shown in FIG. 4b with Forearm Site 1 and the Plasma Glucose.

The results of the testing showed that the determined glucose values using the inventive method (Forearm Sites 1-3) correlated with the subject's parallel glucose values in a comparative method (Plasma Glucose).

Example 2

In Example 2, two different inventive compositions were made. In Inventive Hydrogel Pad 1, a copolymeric network and a cellulose matrix were grafted together. In Inventive Hydrogel Pad 2, a copolymeric network was formed and then placed onto a nylon mesh.

Specifically, in Inventive Hydrogel Pad 1, a copolymeric network and a cellulose matrix were grafted together. The copolymeric network comprised 60 parts of N-vinyl pyrrolidone (first monomer), 40 parts of vinyl acetate (second monomer), 1 part of diethylene glycol divinyl ether, and 1 part of (2-hydroxy-4'-(2-hydroxyethoxy)-2-methylpropiopheone, which is an ultraviolet (UV) initiator. The weight ratio of the copolymeric network to the cellulose matrix was 2:1. The cellulose matrix used was Kimwipes® absorbent wipers EX-L from Kimberly-Clark.

The monomer mixture was absorbed into the porous Kimwipes® absorbent wipers EX-L and then exposed to UV radiation for two hours to complete the polymerization reaction. After the reaction, the gelled copolymeric network and the cellulose matrix were immersed in water to remove non-reacted monomers. The cellulose interpenetrated the crosslinked copolymeric network and, thus, were chemically bonded together. The first and second monomers were also chemically bonded to each other.

The chemically-bonded copolymeric/cellulose network were fully hydrated with water to form a hydrogel sheet. After being fully hydrated, a buffer with an enzyme (glucose oxidase) was added to the hydrogel sheet. The hydrogel sheet was then dried and stored.

The hydrogel sheet was cut into a desired size to form a hydrogel pad. The hydrogel pad was attached to a surface of an electrochemical sensor. The attached hydrogel pad was then re-hydrated with water, which included a buffer. Inventive Hydrogel Pad 1 was from about 60 to about 90 wt. % water, and was generally uniform and mechanically stable.

The skin was treated with ultrasound energy using the Sontra SonoPrep® ultrasonic skin permeation system. Tests were performed on two different areas of the skin—the wrist and elbow. Inventive Hydrogel Pad 1 was adhered to the skin at each of these locations. The current was measured by the electrochemical sensor and a glucose concentration was determined at each location.

Inventive Hydrogel Pad 2 comprised a copolymeric network. The copolymeric network comprised 60 parts of N-vinyl pyrrolidone (first monomer), 40 parts of vinyl acetate (second monomer), 1 part of diethylene glycol divinyl ether, and 1 part of (2-hydroxy-4'-(2-hydroxyethoxy)-2-methylpropiopheone. The copolymeric network was exposed to UV radiation for two hours to complete the polymerization reaction. After the reaction, the gelled copolymeric network was immersed in water to remove non-reacted monomers. The first and second monomers were chemically bonded to each other.

The copolymeric network was fully hydrated with water to form a hydrogel sheet. After being fully hydrated, a buffer with an enzyme (glucose oxidase) was added to the hydrogel sheet. The hydrogel sheet was then dried and stored. To improve the handling of the hydrogel sheet, a nylon mesh was used to support the hydrogel sheet. The hydrogel sheet with nylon mesh was cut into a desired size to form Inventive Hydrogel Pad 2. Inventive Hydrogel Pad 2 was attached to a surface of an electrochemical sensor. The attached Inventive Hydrogel Pad 2 was then re-hydrated with water, which included a buffer. The hydrated Inventive Hydrogel Pad 2 comprised from about 60 to about 90 wt. % water and was generally uniform and mechanically stable.

The skin (forearm) was treated with ultrasound energy using the Sontra SonoPrep® ultrasonic skin permeation system. The hydrated Inventive Hydrogel Pad 2 was adhered to the skin (forearm). The current was measured by the electrochemical sensor and a glucose concentration was determined.

Figure 5:
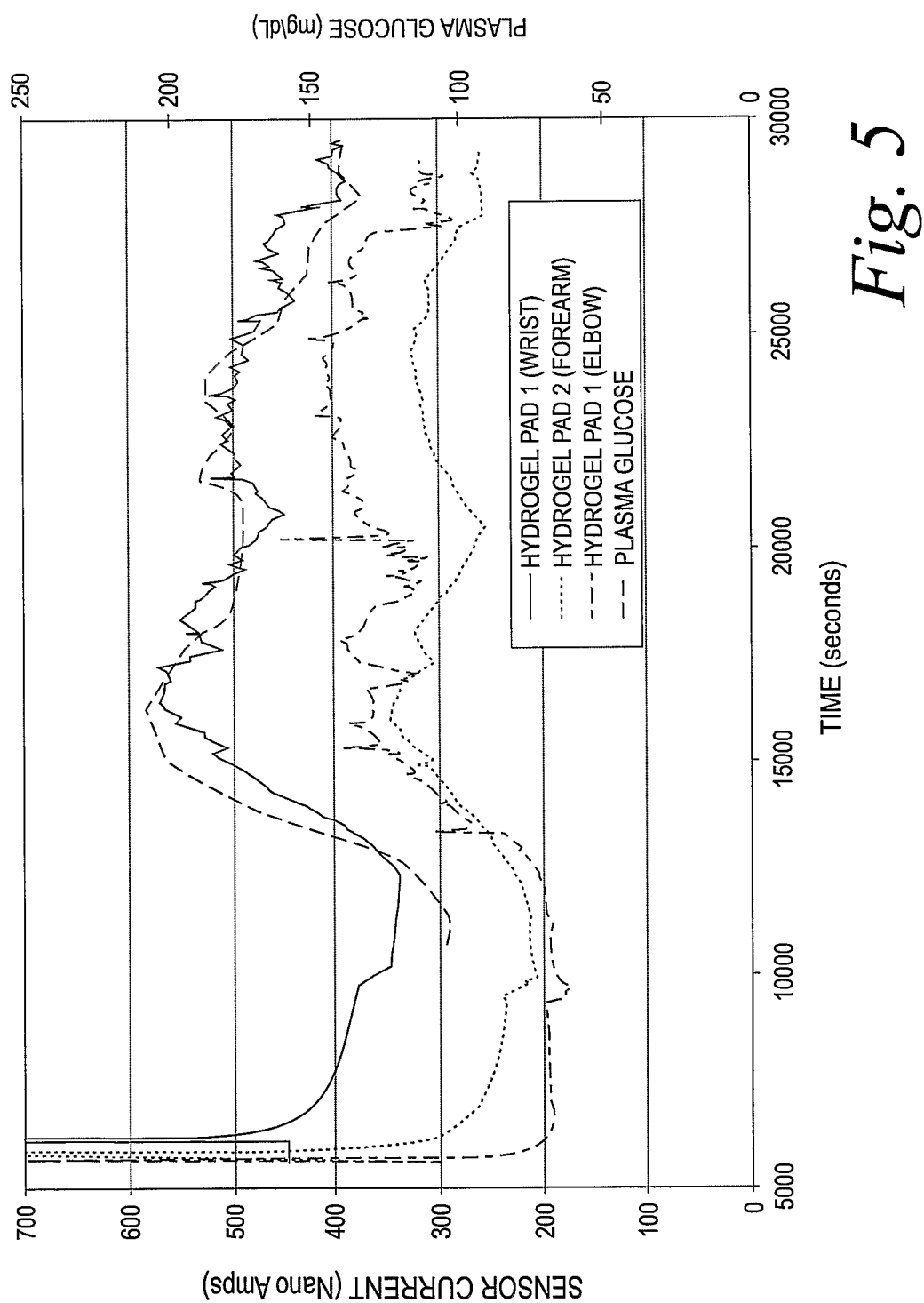
FIG. 5 is a graph plotting current, glucose concentration versus time.

The results of the testing using Inventive Hydrogel Pads 1 and 2 are shown in FIG. 5. FIG. 5 plots current (nano amps) and glucose concentration (mg/dL) versus time. Specifically, FIG. 5 depicts the Comparative Method (labeled Plasma Glucose in FIG. 5) that tested the blood and measured the glucose concentration using an electrochemical sensor. The Comparative Method of FIG. 5 did not use a hydrogel composition. In the Comparative Method, blood samples were taken every 30 minutes and analyzed with an Analox GM9D Analyzer, which is marketed by Analox Instruments U.S.A., Inc. of Lunenberg, Mass. The results of the methods using the Inventive Hydrogel Pad 1 (at both the wrist and elbow) and the Hydrogel Pad 2 (forearm) were also plotted. As shown in FIG. 5, the glucose concentrations from the inventive methods (using Inventive Hydrogel Pads 1 and 2) generally correlated with the subject's plasma glucose concentrations from Comparative Method 1.

Alternative Embodiment A

A hydrogel composition comprising a first monomer, a second monomer, a cross-linking agent, and a solvent, the first monomer being selected from Formula I:

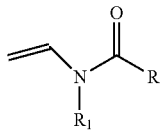

Formula I wherein
R and R1 are independently selected from H, $(C_1-C_3)$alkyl, $(C_3-C_6)$dihydroxy alkyl and $(C_2-C_6)$hydroxy alkyl; or the combination of R and R1 is selected from 1 carbon to 5 carbon atoms such that a 3-7 member heterocyclic moiety is formed;

the second monomer being selected from the group consisting of Formula II and Formula III, wherein Formula II is

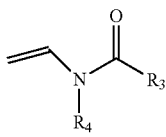

Formula II wherein
R3 and R4 are independently selected from H, $CH_3$, $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, with the proviso that when R3 is H or $CH_3$, then R4 is $(C_3-C_{18})$alkyl, $(C_3-C_7)$cycloalkyl or an aromatic moiety, wherein the alkyl, cycloalkyl or aromatic moiety is optionally substituted with one or more substituents, with the proviso that when R4 is H or $CH_3$, then R3 is $(C_3-C_{18})$alkyl, $(C_3-C_7)$cycloalkyl or an aromatic moiety, wherein the alkyl, cycloalkyl or aromatic moiety is optionally substituted with one or more substituents; and wherein Formula III is

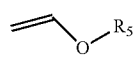

Formula III wherein
R5 is selected from $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein the ratio of the first monomer to the second monomer is from about 0.1:99.9 to about 99.9:0.1.

Alternative Embodiment B

The hydrogel composition of Alternative Embodiment A wherein the cross-linking agent is a multifunctional vinyl ether, a divinylbenzene, a multifunctional acrylate, or a multifunctional acrylamide.

Alternative Embodiment C

The hydrogel composition of Alternative Embodiment B wherein the cross-linking agent is a multifunctional vinyl ether, the multifunctional vinyl ether being a diethylene glycol divinyl ether acrylate, triethylene glycol divinyl ether, and tetra(ethylene glycol) divinyl ether.

Alternative Embodiment D

The hydrogel composition of Alternative Embodiment B wherein the cross-linking agent is a divinylbenzene.

Alternative Embodiment E

The hydrogel composition of Alternative Embodiment B wherein the cross-linking agent is a multifunctional acrylate, the multifunctional acrylate being ethylene glycol dimethacrylate (EGDMA), polyethylene glycol diacrylates, diethylene glycol dimethacrylate, diethylene glycol diacrylate, ethylene glycol diacrylate, or 1,3-dihydroxypropyldimethacrylate.

Alternative Embodiment F

The hydrogel composition of Alternative Embodiment B wherein the cross-linking agent is a multifunctional acrylamide.

Alternative Embodiment G

The hydrogel composition of Alternative Embodiment A wherein the solvent is water.

Alternative Embodiment H

The hydrogel composition of Alternative Embodiment A further including a photo-initiator.

Alternative Embodiment I

The hydrogel composition of Alternative Embodiment A wherein the ratio of the first monomer to the second monomer is from about 20:80 to about 80:20.

Alternative Embodiment J

The hydrogel composition of Alternative Embodiment A wherein the second monomer is selected from Formula II.

Alternative Embodiment K

The hydrogel composition of Alternative Embodiment A wherein the second monomer is selected from Formula III.

Alternative Embodiment L

The hydrogel composition of Alternative Embodiment A wherein the first monomer is N-vinyl acetamide, N-vinyl propionamide, N-vinyl pyrrolidone or N-vinyl caprolactam, the second monomer being selected from Formula II with R3 or R4 being a ($C_3$-$C_{18}$)alkyl that is optionally substituted.

Alternative Embodiment M

The hydrogel composition of Alternative Embodiment A wherein the first monomer is N-vinyl acetamide, N-vinyl propionamide, N-vinyl pyrrolidone or N-vinyl caprolactam, the second monomer being selected from Formula II with R3 or R4 being a ($C_3$-$C_7$)cycloalkyl that is optionally substituted.

Alternative Embodiment N

The hydrogel composition of Alternative Embodiment A wherein the first monomer is N-vinyl acetamide, N-vinyl propionamide, N-vinyl pyrrolidone or N-vinyl caprolactam, the second monomer being selected from Formula II with R3 or R4 being an aromatic moiety that is optionally substituted.

Alternative Embodiment O

The hydrogel composition of Alternative Embodiment A wherein the first monomer is N-vinyl acetamide, N-vinyl propionamide, N-vinyl pyrrolidone or N-vinyl caprolactam, the second monomer being selected from Formula III with R3 or R4 being a ($C_3$-$C_{18}$)alkyl that is optionally substituted.

Alternative Embodiment P

The hydrogel composition of Alternative Embodiment A wherein the first monomer is N-vinyl acetamide, N-vinyl propionamide, N-vinyl pyrrolidone or N-vinyl caprolactam, the second monomer being selected from Formula III with R3 or R4 being a ($C_3$-$C_7$)cycloalkyl that is optionally substituted.

Alternative Embodiment Q

The hydrogel composition of Alternative Embodiment A wherein the first monomer is N-vinyl acetamide, N-vinyl propionamide, N-vinyl pyrrolidone or N-vinyl caprolactam, the second monomer being selected from Formula III with R3 or R4 being an aromatic moiety that is optionally substituted.

Alternative Embodiment R

An electrochemical sensor system comprising:
an electrochemical sensor having at least a counter electrode and a working electrode; and
a hydrogel composition contacting the working electrode, the hydrogel composition comprising a first monomer, a second monomer, a cross-linking agent, and a solvent, the first monomer being selected from hydroxy alkyl methacrylates, acrylamide, N,N di-alkyl acrylamides, methacrylic acid, acrylic acid, methacrylate metal salts, acrylate metal salts, iticonic acid, maleic acid, methacrylamide, N,N-dialkylacrylamide, styrene sulfonic acid, styrene sulfonate metal salts, styrene carboxylic acid, styrene carboxylate metal salts, acrylamido-2-methylpropane sulfonic acid, acrylamido-2-methylpropane sulfonate metal salts, 2-vinyl N-alkylpyridinium halide, 4-vinyl N-alkylpyridinium halide, or Formula I, wherein Formula I is

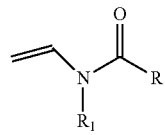

Formula I wherein
R and R1 are independently selected from H, ($C_1$-$C_3$)alkyl, ($C_3$-$C_6$)dihydroxy alkyl and ($C_2$-$C_6$)hydroxy alkyl; or
the combination of R and R1 is selected from 1 carbon to 5 carbon atoms such that a 3-7 member heterocyclic moiety is formed;
the second monomer being selected from the group consisting of alkyl (meth)acrylates, Formula II, Formula III, and Formula IV, wherein Formula II is

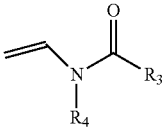

Formula II wherein
R3 and R4 are independently selected from H, $CH_3$, ($C_3$-$C_{18}$)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;
($C_3$-$C_7$)cycloalkyl, wherein the cycloalkyl is optionally substituted with one or more substituents selected from alkyls, halos, haloalkyls, cycloalkyls, nitros, and cyanos; and
aromatic moieties, wherein the aromatic moieties are optionally substituted with one or more substituents selected from alkyls, halos, haloalkyls, cycloalkyls, nitros, and cyanos, with the proviso that when R3 is H or CH₃, then R4 is (C₃-C₁₈)alkyl, (C₃-C₇)cycloalkyl or an aromatic moiety, wherein the alkyl, cycloalkyl or aromatic moiety is optionally substituted with one or more substituents, with the proviso that when R4 is H or CH₃, then R3 is (C₃-C₁₈)alkyl, (C₃-C₇)cycloalkyl or an aromatic moiety, wherein the alkyl, cycloalkyl or aromatic moiety is optionally substituted with one or more substituents; and wherein Formula III is

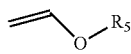

Formula III wherein

R5 is selected from (C₃-C₁₈)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

(C₃-C₇)cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein Formula IV is

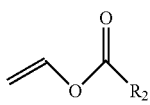

Formula IV wherein

R2 is selected from (C₁-C₁₈)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

(C₃-C₇)cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein the ratio of the first monomer to the second monomer is from about 0.1:99.9 to about 99.9:0.1.

Alternative Embodiment S

The electrochemical sensor system of Alternative Embodiment R further including an adhesive structure securing the hydrogel composition to the electrochemical sensor.

Alternative Embodiment T

The electrochemical sensor system of Alternative Embodiment R wherein the electrochemical sensor further includes a reference electrode.

Alternative Embodiment U

The electrochemical sensor system of Alternative Embodiment R wherein the hydrogel composition is a dried hydrogel composition.

Alternative Embodiment V

The electrochemical sensor system of Alternative Embodiment U wherein the dried hydrogel composition is a film.

Alternative Embodiment W

The electrochemical sensor system of Alternative Embodiment R further including a mechanical support to assist in providing mechanical strength to the hydrogel composition.

Alternative Embodiment X

The electrochemical sensor system of Alternative Embodiment W wherein the mechanical support is polymeric mesh, woven fabric, non-woven fabric, cellulose, or combinations thereof.

Alternative Embodiment Y

The electrochemical sensor system of Alternative Embodiment R wherein the hydrogel composition has a thickness of from about 0.1 mil to about 100 mils.

Alternative Embodiment Z

The electrochemical sensor system of Alternative Embodiment Y wherein the hydrogel composition has a thickness of from about 1 mil to about 30 mils.

Alternative Embodiment AA

The electrochemical sensor system of Alternative Embodiment R wherein the ratio of the first monomer to the second monomer is from about 20:80 to about 80:20.

Alternative Embodiment BB

An electrochemical sensor system comprising:
an electrochemical sensor having at least a counter electrode and a working electrode; and
a hydrogel composition contacting the working electrode, the hydrogel composition comprising a first monomer, a second monomer, a cross-linking agent, and a solvent, the first monomer being selected from Formula I

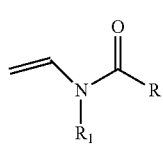

Formula I wherein
R and R1 are independently selected from H, $(C_1-C_3)$alkyl, $(C_3-C_6)$dihydroxy alkyl and $(C_2-C_6)$hydroxy alkyl; or
the combination of R and R1 is selected from 1 carbon to 5 carbon atoms such that a 3-7 member heterocyclic moiety is formed;
the second monomer being selected from the group consisting of alkyl (meth)acrylates, Formula II, Formula III, and Formula IV, wherein Formula II is

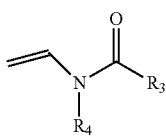

Formula II wherein
R3 and R4 are independently selected from H, $CH_3$, $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, with the proviso that when R3 is H or $CH_3$, then R4 is $(C_3-C_{18})$alkyl, $(C_3-C_7)$cycloalkyl or an aromatic moiety, wherein the alkyl, cycloalkyl or aromatic moiety is optionally substituted with one or more substituents, with the proviso that when R4 is H or $CH_3$, then R3 is $(C_3-C_{18})$alkyl, $(C_3-C_7)$cycloalkyl or an aromatic moiety, wherein the alkyl, cycloalkyl or aromatic moiety is optionally substituted with one or more substituents; and wherein Formula III is

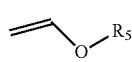

Formula III wherein
R5 is selected from $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein Formula IV is

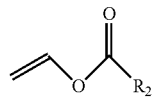

Formula IV wherein
R2 is selected from $(C_1-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein the ratio of the first monomer to the second monomer is from about 0.1:99.9 to about 99.9:0.1.

Alternative Embodiment CC

The electrochemical sensor system of Alternative Embodiment BB further including an adhesive structure securing the hydrogel composition to the electrochemical sensor.

Alternative Embodiment DD

The electrochemical sensor system of Alternative Embodiment BB wherein the electrochemical sensor further includes a reference electrode.

Alternative Embodiment Ee

The electrochemical sensor system of Alternative Embodiment BB wherein the hydrogel composition is a dried hydrogel composition.

Alternative Embodiment FF

The electrochemical sensor system of Alternative Embodiment EE wherein the dried hydrogel composition is a film.

Alternative Embodiment GG

The electrochemical sensor system of Alternative Embodiment BB further including a mechanical support to assist in providing mechanical strength to the hydrogel composition.

Alternative Embodiment HH

The electrochemical sensor system of Alternative Embodiment GG wherein the mechanical support is polymeric mesh, woven fabric, non-woven fabric, paper, or combinations thereof.

Alternative Embodiment II

The electrochemical sensor system of Alternative Embodiment BB wherein the cross-linking agent is a mul-

Alternative Embodiment JJ

The electrochemical sensor system of Alternative Embodiment BB wherein the ratio of the first monomer to the second monomer is from about 20:80 to about 80:20.

Alternative Embodiment KK

An electrochemical sensor system comprising:
an electrochemical sensor having at least a counter electrode and a working electrode; and
a hydrogel composition contacting the working electrode, the hydrogel composition comprising a first monomer, a second monomer, a cross-linking agent, and a solvent, the first monomer being selected from the group consisting of N-vinyl pyrrolidone, hydroxy alkyl methacrylates, acrylamide, and N,N di-alkyl acrylamides, the second monomer being selected from the group consisting of alkyl (meth) acrylates, N-vinyl acrylamide, vinyl esters, and vinyl ethers, and wherein the ratio of the first monomer to the second monomer is from about 0.1:99.9 to about 99.9:0.1.

Alternative Embodiment LL

The electrochemical sensor system of Alternative Embodiment KK further including an adhesive structure securing the hydrogel composition to the electrochemical sensor.

Alternative Embodiment MM

The electrochemical sensor system of Alternative Embodiment KK wherein the electrochemical sensor further includes a reference electrode.

Alternative Embodiment NN

The electrochemical sensor system of Alternative Embodiment KK wherein the hydrogel composition is a dried hydrogel composition.

Alternative Embodiment OO

The electrochemical sensor system of Alternative Embodiment NN wherein the dried hydrogel composition is a film.

Alternative Embodiment PP

The electrochemical sensor system of Alternative Embodiment KK further including a mechanical support to assist in providing mechanical strength to the hydrogel composition.

Alternative Embodiment QQ

The electrochemical sensor system of Alternative Embodiment PP wherein the mechanical support is polymeric mesh, woven fabric, non-woven fabric, paper, or combinations thereof.

Alternative Embodiment RR

The electrochemical sensor system of Alternative Embodiment KK wherein the first monomer is N-vinyl pyrrolidone and the second monomer is a vinyl ester.

Alternative Embodiment SS

The electrochemical sensor system of Alternative Embodiment KK wherein the cross-linking agent is a multifunctional vinyl ether, a divinylbenzene, a multifunctional acrylate, or a multifunctional acrylamide.

Alternative Embodiment TT

The electrochemical sensor system of Alternative Embodiment KK wherein the ratio of the first monomer to the second monomer is from about 20:80 to about 80:20.

Alternative Embodiment UU

An electrochemical sensor system comprising:
an electrochemical sensor having at least a counter electrode and a working electrode; and
a hydrogel composition contacting the working electrode, the hydrogel composition comprising a first monomer, a second monomer, a cross-linking agent, and a solvent, the first monomer having hydrophilic characteristics, the second monomer having hydrophobic characteristics, and wherein the ratio of the first monomer to the second monomer is from about 0.1:99.9 to about 99.9:0.1.

Alternative Process A

A method of determining an analyte concentration, the method comprising the acts of:
placing a hydrogel composition on skin, the hydrogel composition comprising a first monomer, a second monomer, a cross-linking agent, and a solvent, the first monomer being selected from hydroxy alkyl methacrylates, acrylamide, N,N di-alkyl acrylamides, methacrylic acid, acrylic acid, methacrylate metal salts, acrylate metal salts, iticonic acid, maleic acid, methacrylamide, N,N-dialkylacrylamide, styrene sulfonic acid, styrene sulfonate metal salts, styrene carboxylic acid, styrene carboxylate metal salts, acrylamido-2-methylpropane sulfonic acid, acrylamido-2-methylpropane sulfonate metal salts, 2-vinyl N-alkylpyridinium halide, 4-vinyl N-alkylpyridinium halide, or Formula I, wherein Formula I is

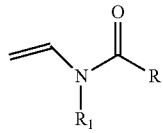

Formula I wherein
R and R1 are independently selected from H, $(C_1-C_3)$alkyl, $(C_3-C_6)$dihydroxy alkyl and $(C_2-C_6)$hydroxy alkyl; or
the combination of R and R1 is selected from 1 carbon to 5 carbon atoms such that a 3-7 member heterocyclic moiety is formed;
the second monomer being selected from the group consisting of alkyl (meth)acrylates, Formula II, Formula III, and Formula IV, wherein Formula II is

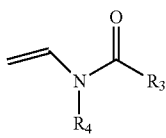

Formula II wherein
R3 and R4 are independently selected from H, CH$_3$, (C$_3$-C$_{18}$)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

(C$_3$-C$_7$)cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, with the proviso that when R3 is H or CH$_3$, then R4 is (C$_3$-C$_{18}$)alkyl, (C$_3$-C$_7$)cycloalkyl or an aromatic moiety, wherein the alkyl, cycloalkyl or aromatic moiety is optionally substituted with one or more substituents, with the proviso that when R4 is H or CH$_3$, then R3 is (C$_3$-C$_{18}$)alkyl, (C$_3$-C$_7$)cycloalkyl or an aromatic moiety, wherein the alkyl, cycloalkyl or aromatic moiety is optionally substituted with one or more substituents; and
wherein Formula III is

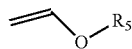

Formula III wherein
R5 is selected from (C$_3$-C$_{18}$)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

(C$_3$-C$_7$)cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos,
wherein Formula IV is

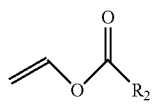

Formula IV wherein
R2 is selected from (C$_1$-C$_{18}$)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

(C$_3$-C$_7$)cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein the ratio of the first monomer to the second monomer is from about 0.1:99.9 to about 99.9:0.1;

providing a sensor, the hydrogel composition located generally between and coupling the skin and the sensor; and sampling of the interstitial fluid to determine the analyte concentration using the sensor.

Alternative Process B

The method of Alternative Process A further including pre-treating the skin to improve permeability of the skin.

Alternative Process C

The method of Alternative Process B wherein the pre-treating includes applying ultrasound energy to the skin.

Alternative Process D

The method of Alternative Process A wherein the skin is the volar forearm.

Alternative Process E

The method of Alternative Process A wherein the analyte is glucose.

Alternative Process F

The method of Alternative Process A wherein the sensor is an electrochemical sensor.

Alternative Process G

The method of Alternative Process A wherein the ratio of the first monomer to the second monomer is from about 20:80 to about 80:20.

Alternative Process H

A method of determining an analyte concentration, the method comprising the acts of:
placing a hydrogel composition on skin, the hydrogel composition comprising a first monomer, a second monomer, a cross-linking agent, and a solvent, the first monomer being selected from Formula I

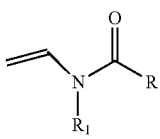

Formula I wherein

R and R1 are independently selected from H, $(C_1-C_3)$alkyl, $(C_3-C_6)$dihydroxy alkyl and $(C_2-C_6)$hydroxy alkyl; or the combination of R and R1 is selected from 1 carbon to 5 carbon atoms such that a 3-7 member heterocyclic moiety is formed;

the second monomer being selected from the group consisting of alkyl (meth)acrylates, Formula II, Formula III, and Formula IV, wherein Formula II is

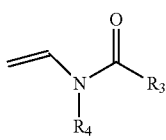

Formula II wherein

R3 and R4 are independently selected from H, $CH_3$, $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, with the proviso that when R3 is H or $CH_3$, then R4 is $(C_3-C_{18})$alkyl, $(C_3-C_7)$cycloalkyl or an aromatic moiety, wherein the alkyl, cycloalkyl or aromatic moiety is optionally substituted with one or more substituents, with the proviso that when R4 is H or $CH_3$, then R3 is $(C_3-C_{18})$alkyl, $(C_3-C_7)$cycloalkyl or an aromatic moiety, wherein the alkyl, cycloalkyl or aromatic moiety is optionally substituted with one or more substituents; and wherein Formula III is

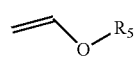

Formula III wherein

R5 is selected from $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein Formula IV is

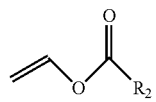

Formula IV wherein

R2 is selected from $(C_1-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, wherein the ratio of the first monomer to the second monomer is from about 0.1:99.9 to about 99.9:0.1;

providing a sensor, the hydrogel composition located generally between and coupling the skin and the sensor; and sampling of the interstitial fluid to determine the analyte concentration using the sensor.

Alternative Process I

The method of Alternative Process H further including pre-treating the skin to improve permeability of the skin.

Alternative Process J

The method of Alternative Process I wherein the pre-treating includes applying ultrasound energy to the skin.

Alternative Process K

The method of Alternative Process H wherein the skin is the volar forearm.

Alternative Process L

The method of Alternative Process H wherein the analyte is glucose.

Alternative Process M

The method of Alternative Process H wherein the sensor is an electrochemical sensor.

Alternative Process N

The method of Alternative Process H wherein the ratio of the first monomer to the second monomer is from about 20:80 to about 80:20.

Alternative Process O

A method of determining an analyte concentration, the method comprising the acts of:

placing a hydrogel composition on skin, the hydrogel composition comprising a first monomer, a second monomer, a cross-linking agent, and a solvent, the first monomer being selected from the group consisting of N-vinyl pyrrolidone, hydroxy alkyl methacrylates, acrylamide, and N,N di-alkyl acrylamides, the second monomer being selected from the group consisting of alkyl (meth)acrylates, N-vinyl acylamide, vinyl esters, and vinyl ethers, and wherein the ratio of the first monomer to the second monomer is from about 0.1:99.9 to about 99.9:0.1;

providing a sensor, the hydrogel composition located generally between and coupling the skin and the sensor; and sampling of the interstitial fluid to determine the analyte concentration using the sensor.

Alternative Process P

The method of Alternative Process O further including pre-treating the skin to improve permeability of the skin.

Alternative Process Q

The method of Alternative Process P wherein the pre-treating includes applying ultrasound energy to the skin.

Alternative Process R

The method of Alternative Process O wherein the skin is the volar forearm.

Alternative Process S

The method of Alternative Process O wherein the analyte is glucose.

Alternative Process T

The method of Alternative Process O wherein the sensor is an electrochemical sensor.

Alternative Process U

The method of Alternative Process O wherein the first monomer is N-vinyl pyrrolidone and the second monomer is a vinyl ester.

Alternative Process V

The method of Alternative Process U wherein the cross-linking agent is a multifunctional vinyl ether, a divinylbenzene, a multifunctional acrylate, or a multifunctional acrylamide.

Alternative Process W

The method of Alternative Process O wherein the ratio of the first monomer to the second monomer is from about 20:80 to about 80:20.

Alternative Process X

A method of determining an analyte concentration, the method comprising the acts of:

placing a hydrogel composition on skin, the hydrogel composition comprising a first monomer, a second monomer, a cross-linking agent, and a solvent, the first monomer having hydrophilic characteristics, the second monomer having hydrophobic characteristics, wherein the ratio of the first monomer to the second monomer is from about 0.1:99.9 to about 99.9:0.1;

providing a sensor, the hydrogel composition located generally between and coupling the skin and the sensor; and sampling of the interstitial fluid to determine the analyte concentration using the sensor.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

The invention claimed is:

1. A method of determining an analyte concentration, the method comprising the acts of:

placing a hydrogel composition on skin, the hydrogel composition comprising a first monomer, a second monomer, a cross-linking agent, and a solvent, the first monomer being selected from Formula I

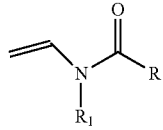

Formula I wherein the combination of R and R1 is selected from 1 carbon to 5 carbon atoms such that a 3-7 member heterocyclic moiety is formed;

the second monomer being selected from Formula II, wherein Formula II is

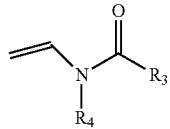

Formula II wherein R3 and R4 are independently selected from H, $CH_3$, $(C_3-C_{18})$alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

$(C_3-C_7)$cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, with the proviso that when R3 is H or $CH_3$, then R4 is $(C_3-C_{18})$alkyl, $(C_3-C_7)$cycloalkyl or an aromatic moiety, wherein the alkyl, cycloalkyl or aromatic moiety is optionally substituted with one or more substituents, with the proviso that when R4 is H or $CH_3$, then R3 is $(C_3-C_{18})$alkyl, $(C_3-C_7)$cycloalkyl or an aromatic moiety, wherein the alkyl, cycloalkyl or aromatic moiety is optionally substituted with one or more substituents;

wherein the ratio of the first monomer to the second monomer is from about 20:80 to about 80:20;

providing a sensor, the hydrogel composition located generally between and coupling the skin and the sensor; and sampling of the interstitial fluid to determine the analyte concentration using the sensor.

2. The method of claim 1, wherein the ratio of the first monomer to the second monomer is from about 40:60 to about 60:40.

3. The method of claim 1, wherein the analyte is glucose.

4. The method of claim 1, wherein the sensor is an electrochemical sensor.

5. The method of claim 1, wherein the first monomer is N-vinyl pyrrolidone.

6. The method of claim 1, wherein the first monomer is N-vinyl caprolactam.

7. The method of claim 1, wherein the first monomer is N-vinyl pyrrolidone, the second monomer of Formula II being a ($C_3$-$C_{18}$)alkyl that is optionally substituted.

8. The method of claim 7, wherein the first monomer is N-vinyl pyrrolidone, the second monomer of Formula II being N-vinyl butyramide, N-vinyl valeramide, N-vinyl lauramide, or N-vinyl 4-chlorobutyramide.

9. The method of claim 1, wherein the second monomer of Formula II is N-vinyl butyramide, N-vinyl valeramide, N-vinyl lauramide, or N-vinyl 4-chlorobutyramide.

10. The method of claim 1, wherein the first monomer is N-vinyl caprolactam, the second monomer of Formula II being a ($C_3$-$C_{18}$)alkyl that is optionally substituted.

11. The method of claim 10, wherein the first monomer is N-vinyl caprolactam, the second monomer of Formula II being N-vinyl butyramide, N-vinyl valeramide, N-vinyl lauramide, or N-vinyl 4-chlorobutyramide.

12. The method of claim 1, wherein the first monomer is N-vinyl pyrrolidone, the second monomer of Formula II being a ($C_3$-$C_7$) cycloalkyl that is optionally substituted.

13. The method of claim 12, wherein the first monomer is N-vinyl pyrrolidone, the second monomer of Formula II being N-vinyl cyclohexylcarboxamide, N-vinyl cyclopentylcarboamide, or N-vinyl 4-bromocyclohexylcarboxamide.

14. The method of claim 1, wherein the second monomer of Formula II is N-vinyl cyclohexylcarboxamide, N-vinyl cyclopentylcarboamide, or N-vinyl 4-bromocyclohexylcarboxamide.

15. The method of claim 1, wherein the first monomer is N-vinyl caprolactam, the second monomer of Formula II being a ($C_3$-$C_7$) cycloalkyl that is optionally substituted.

16. The method of claim 15, wherein the first monomer is N-vinyl caprolactam, the second monomer of Formula II being N-vinyl cyclohexylcarboxamide, N-vinyl cyclopentylcarboamide, or N-vinyl 4-bromocyclohexylcarboxamide.

17. The method of claim 1, wherein the first monomer is N-vinyl pyrrolidone, the second monomer of Formula II being an aromatic moiety that is optionally substituted.

18. The method of claim 17, wherein the first monomer is N-vinyl pyrrolidone, the second monomer of Formula II being N-vinyl benzamide, N-vinyl 4-nitrobenzamide, or N-vinyl naphthamide.

19. The method of claim 1, wherein the second monomer of Formula II is N-vinyl benzamide, N-vinyl 4-nitrobenzamide, or N-vinyl naphthamide.

20. The method of claim 1, wherein the first monomer is N-vinyl caprolactam, the second monomer of Formula II being an aromatic moiety that is optionally substituted.

21. The method of claim 20, wherein the first monomer is N-vinyl caprolactam, the second monomer of Formula II being N-vinyl benzamide, N-vinyl 4-nitrobenzamide, or N-vinyl naphthamide.

22. The method of claim 1, wherein the hydrogel composition has a thickness of from about 0.1 mil to about 100 mils.

23. The method of claim 1, wherein the hydrogel composition has a thickness of from about 1 mil to about 30 mils.

24. An electrochemical sensor system comprising:
an electrochemical sensor having at least a counter electrode and a working electrode; and
a hydrogel composition contacting the working electrode, the hydrogel composition comprising a first monomer, a second monomer, a cross-linking agent, and a solvent, the first monomer being selected from Formula I

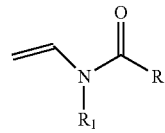

Formula I wherein the combination of R and R1 is selected from 1 carbon to 5 carbon atoms such that a 3-7 member heterocyclic moiety is formed;
the second monomer being selected from Formula II, wherein Formula II is Formula II wherein R3 and R4 are independently selected from H, $CH_3$, ($C_3$-$C_{18}$)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;
($C_3$-$C_7$)cycloalkyl, wherein the cycloalkyl is optionally substituted with one or more substituents selected from alkyls, halos, haloalkyls, cycloalkyls, nitros, and cyanos; and
aromatic moieties, wherein the aromatic moieties are optionally substituted with one or more substituents selected from alkyls, halos, haloalkyls, cycloalkyls, nitros, and cyanos,
with the proviso that when R3 is H or $CH_3$, then R4 is ($C_3$-$C_{18}$)alkyl, ($C_3$-$C_7$)cycloalkyl or an aromatic moiety, wherein the alkyl, cycloalkyl or aromatic moiety is optionally substituted with one or more substituents,
with the proviso that when R4 is H or $CH_3$, then R3 is ($C_3$-$C_{18}$)alkyl, ($C_3$-$C_7$)cycloalkyl or an aromatic moiety, wherein the alkyl, cycloalkyl or aromatic moiety is optionally substituted with one or more substituents; and
wherein the ratio of the first monomer to the second monomer is from about 20:80 to about 80:20.

25. The electrochemical sensor system of claim 24, wherein the ratio of the first monomer to the second monomer is from about 40:60 to about 60:40.

26. The electrochemical sensor system of claim 24, wherein the analyte is glucose.

27. The electrochemical sensor system of claim 24, wherein the first monomer is N-vinyl pyrrolidone.

28. The electrochemical sensor system of claim 24, wherein the first monomer is N-vinyl caprolactam.

29. The electrochemical sensor system of claim 24, wherein the second monomer of Formula II being a ($C_3$-$C_{18}$)alkyl that is optionally substituted.

30. The electrochemical sensor system of claim 29, wherein the second monomer of Formula II is N-vinyl butyramide, N-vinyl valeramide, N-vinyl lauramide, or N-vinyl 4-chlorobutyramide.

31. The electrochemical sensor system of claim 24, wherein the second monomer of Formula II is a ($C_3$-$C_7$) cycloalkyl that is optionally substituted.

32. The electrochemical sensor system of claim 31, wherein the second monomer of Formula II is N-vinyl cyclohexylcarboxamide, N-vinyl cyclopentylcarboamide, or N-vinyl 4-bromocyclohexylcarboxamide.

33. The electrochemical sensor system of claim 24, wherein the second monomer of Formula II is an aromatic moiety that is optionally substituted.

34. The electrochemical sensor system of claim 33, wherein the second monomer of Formula II is N-vinyl benzamide, N-vinyl 4-nitrobenzamide, or N-vinyl naphthamide.

35. The electrochemical sensor system of claim 24, further including a mechanical support to assist in providing mechanical strength to the hydrogel composition.

36. The electrochemical sensor system of claim 24, wherein the hydrogel composition has a thickness of from about 0.1 mil to about 100 mils.

37. The electrochemical sensor system of claim 36, wherein the hydrogel composition has a thickness of from about 1 mil to about 30 mils.

38. An electrochemical sensor system comprising:
an electrochemical sensor having at least a counter electrode and a working electrode; and
a hydrogel composition contacting the working electrode, the hydrogel composition comprising a first monomer, a second monomer, a cross-linking agent, and a solvent, the first monomer being selected from Formula I

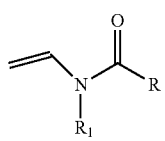

Formula I wherein the combination of R and R1 is selected from 1 carbon to 5 carbon atoms such that a 3-7 member heterocyclic moiety is formed, the first monomer being N-vinyl pyrrolidone or N-vinyl caprolactam;

the second monomer being selected from Formula II, wherein Formula II is

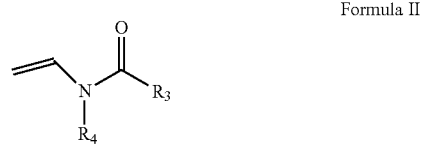

Formula II wherein R3 and R4 are independently selected from H, $CH_3$, ($C_3$-$C_{18}$)alkyl, wherein the alkyl is optionally substituted with one or more substituents selected from halos, haloalkyls, cycloalkyls, nitros, cyanos, 4-8 member heterocyclic moieties, wherein the heterocyclic moieties are optionally substituted with one or more alkyls, halos, haloalkyls, cycloalkyls, nitros, and cyanos;

($C_3$-$C_7$)cycloalkyl, wherein the cycloalkyl is optionally substituted with one or more substituents selected from alkyls, halos, haloalkyls, cycloalkyls, nitros, and cyanos; and aromatic moieties, wherein the aromatic moieties are optionally substituted with one or more substituents selected from alkyls, halos, haloalkyls, cycloalkyls, nitros, and cyanos, with the proviso that when R3 is H or $CH_3$, then R4 is ($C_3$-$C_{18}$)alkyl, ($C_3$-$C_7$)cycloalkyl or an aromatic moiety, wherein the alkyl, cycloalkyl or aromatic moiety is optionally substituted with one or more substituents, with the proviso that when R4 is H or $CH_3$, then R3 is ($C_3$-$C_{18}$)alkyl, ($C_3$-$C_7$)cycloalkyl or an aromatic moiety, wherein the alkyl, cycloalkyl or aromatic moiety is optionally substituted with one or more substituents; and wherein the ratio of the first monomer to the second monomer is from about 20:80 to about 80:20.

* * * * *